(12) United States Patent
Thomas et al.

(10) Patent No.: US 10,271,862 B2
(45) Date of Patent: *Apr. 30, 2019

(54) SURGICAL INSTRUMENTS AND METHODS OF SURGICALLY PREPARING A PATIENT'S TIBIA

(71) Applicant: DEPUY IRELAND UNLIMITED COMPANY, Cork (IE)

(72) Inventors: Kyle B. Thomas, Denver, CO (US); Todd A. Kilpela, Richfield, MN (US); Steven P. Gowers, Cambridge (GB); Ryan C. Keefer, Warsaw, IN (US); William R. Macumber, Edwardsburg, MI (US); Jonathan C. Lee, Mishawaka, IN (US); Lisa M. Robertson, Warsaw, IN (US)

(73) Assignee: DEPUY IRELAND UNLIMITED COMPANY, Ringaskiddy, Co Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/973,684

(22) Filed: May 8, 2018

(65) Prior Publication Data

US 2018/0250023 A1 Sep. 6, 2018

Related U.S. Application Data

(63) Continuation of application No. 15/445,109, filed on Feb. 28, 2017, now Pat. No. 9,962,173, which is a
(Continued)

(51) Int. Cl.
*A61B 17/17* (2006.01)
*A61F 2/46* (2006.01)
(Continued)

(52) U.S. Cl.
CPC ........ *A61B 17/1764* (2013.01); *A61B 17/157* (2013.01); *A61B 17/164* (2013.01);
(Continued)

(58) Field of Classification Search
CPC ..... A61B 17/16; A61B 17/17; A61B 17/1764; A61F 2/38; A61F 2/389
See application file for complete search history.

(56) References Cited

U.S. PATENT DOCUMENTS

| 4,952,213 A | 8/1990 | Bowman et al. |
| 5,356,414 A | 10/1994 | Cohen et al. |

(Continued)

FOREIGN PATENT DOCUMENTS

| CN | 101742972 A | 6/2010 |
| CN | 101849864 A | 10/2010 |

(Continued)

OTHER PUBLICATIONS

Japanese Search Report, Japanese Application No. 2017-210419, dated Jul. 4, 2018, 3 pages.

(Continued)

*Primary Examiner* — Christopher J Beccia
(74) *Attorney, Agent, or Firm* — Barnes & Thornburg LLP

(57) ABSTRACT

A method of surgically preparing a proximal end of a tibia includes inserting an intramedullary orthopedic surgical instrument into a medullary canal of the tibia, securing an attachment device to the intramedullary orthopedic surgical instrument, attaching a cutting block to the attachment device, resecting the proximal end of the tibia using the cutting block to form a surgically-prepared surface, positioning a tibial base trial on the surgically-prepared surface,
(Continued)

and inserting a keel punch through a slot defined in the tibial base trial and into the surgically-prepared surface of the tibia.

8 Claims, 28 Drawing Sheets

Related U.S. Application Data continuation of application No. 14/834,332, filed on Aug. 24, 2015, now Pat. No. 9,579,113, which is a continuation of application No. 13/485,444, filed on May 31, 2012, now Pat. No. 9,113,915.

(60) Provisional application No. 61/653,363, filed on May 30, 2012.

(51) Int. Cl.
| | | |
|---|---|---|
| *A61B 17/15* | (2006.01) | |
| *A61B 17/16* | (2006.01) | |
| *A61F 2/38* | (2006.01) | |
| *A61F 2/30* | (2006.01) | |

(52) U.S. Cl.
CPC ...... *A61B 17/1659* (2013.01); *A61B 17/1675* (2013.01); *A61B 17/1735* (2013.01); *A61F 2/389* (2013.01); *A61F 2/4684* (2013.01); *A61F 2002/30604* (2013.01)

(56) References Cited

U.S. PATENT DOCUMENTS

| | | | |
|---|---|---|---|
| 5,609,642 A | 3/1997 | Johnson et al. | |
| 5,681,316 A | 10/1997 | DeOrio et al. | |
| 5,931,841 A | 8/1999 | Ralph | |
| 5,976,147 A | 11/1999 | LaSalle et al. | |
| 5,989,261 A | 11/1999 | Walker et al. | |
| 6,159,216 A | 12/2000 | Burkinshaw et al. | |
| 7,374,563 B2 * | 5/2008 | Roger | A61B 17/155 606/88 |
| 9,028,501 B2 | 5/2015 | Thomas et al. | |
| 9,095,356 B2 | 8/2015 | Thomas et al. | |
| 9,113,915 B2 | 8/2015 | Thomas et al. | |
| 9,579,113 B2 | 2/2017 | Thomas et al. | |
| 9,962,173 B2 * | 5/2018 | Thomas | A61B 17/157 |
| 2001/0001121 A1 * | 5/2001 | Lombardo | A61B 17/154 606/89 |
| 2004/0087960 A1 | 5/2004 | Kinnett | |
| 2004/0225368 A1 | 11/2004 | Plumet et al. | |
| 2005/0075640 A1 * | 4/2005 | Collazo | A61B 17/1675 606/86 R |
| 2007/0010890 A1 | 1/2007 | Collazo | |
| 2008/0183177 A1 | 7/2008 | Fox et al. | |
| 2008/0228189 A1 | 9/2008 | Fox et al. | |
| 2009/0125114 A1 | 5/2009 | May et al. | |
| 2009/0204115 A1 | 8/2009 | Dees, Jr. et al. | |
| 2009/0222008 A1 | 9/2009 | Hogg et al. | |
| 2010/0121334 A1 | 5/2010 | Couture et al. | |
| 2012/0310246 A1 | 12/2012 | Belcher et al. | |
| 2013/0325014 A1 | 12/2013 | Sordelet et al. | |
| 2013/0325016 A1 | 12/2013 | Sordelet et al. | |
| 2013/0325018 A1 | 12/2013 | Thomas et al. | |
| 2013/0325019 A1 | 12/2013 | Thomas et al. | |
| 2013/0325021 A1 | 12/2013 | Sordelet et al. | |
| 2013/0325136 A1 | 12/2013 | Thomas et al. | |

FOREIGN PATENT DOCUMENTS

| | | | |
|---|---|---|---|
| CN | 101879099 | A | 11/2010 |
| EP | 2145590 | A1 | 1/2010 |
| FR | 2748389 | A1 | 11/1997 |
| FR | 2752519 | A1 | 2/1998 |
| FR | 2943528 | A1 | 10/2010 |
| GB | 2323037 | A | 9/1998 |
| JP | 11500036 | A | 1/1999 |
| JP | 11104155 | A | 4/1999 |
| JP | 2009006066 | A | 1/2009 |
| JP | 2010057527 | A | 3/2010 |
| JP | 6239268 | B2 | 11/2017 |
| WO | 9625123 | A2 | 8/1996 |
| WO | 0013597 | A1 | 3/2000 |
| WO | 2010019284 | A1 | 2/2010 |

OTHER PUBLICATIONS

European Search Report, European Application No. 13169552.0-1654, dated Sep. 4, 2013, 7 pages.
European Search Report, European Application No. 13169544.7-1654, dated Aug. 30, 2013, 7 pages.
European Search Report, European Application No. 13169552.0-1654, dated Oct. 28, 2013, 12 pages.
Zimmer NexGen LCCK, Surgical Technique for use with LCCK 4-in-1 Instrument, 2009, 52 pages.
DePuy Orthopaedics, Inc., Sigma Revision and M.B.T. Revision Tray, Surgical Technique, 2008, 82 pages.
Smith & Nephew, Legion, Revision Knee System, Surgical Technique, 2005, 40 pages.
Biomet, Vanguard SSK, Revision System, Surgical Technique, Feb. 2008, 64 pages.
GMK Revision, Surgical Technique, Ref. 99.27.12US rev. 1, 1999, 74 pages.
PFC Sigma RP-F, Specialist 2 Instruments, Surgical Technique, Performance in Flexion, 2007, 32 pages.
P.F.C. Sigma Rotating Platform Knee System with M.B.T Tray, Primary Procedure with a Curved or Posterior Stablised Implant, 2003, 43 pages.
LCS High Performance Instruments, Surgical Technique, 2008, 44 pages.
Sigma High Performance Instruments, Design Rationale, 2007, 12 pages.
Sigma High Performance Instruments, Classic Surgical Technique, 2010, 52 pages.
Attune Knee System Surgical Technique, 2013, 73 pages.
Declaration of Gary M. Lindsay dated Dec. 23, 2014, 5 pages.
Exhibit A—DePuy Orthopaedics, Inc., Sigma Revision and M.B.T. Revision Tray, Surgical Technique, 2008, 82 pages, previously submitted in IDS filed Apr. 8, 2014.
Exhibit B—Redacted Memorandum with Appendix A, dated Jan. 26, 2010, outlining a surgical instrument evaluation that commenced in 2010, 37 pages.
Exhibit C—"ReInstall Wave 1 Evaluation Surgical Technique," used during the surgical instrument evaluation that commenced in 2010, 36 pages.
Exhibit D—Tray configuration cards showing the instruments used during the surgical instrument evaluation that commenced in 2010, 8 pages.
English translation of Japanese Office Action, Japanese Application No. 2013-112872, dated Mar. 21, 2017, 5 pages.
English translation of Chinese Search Report regarding Chinese Application No. 201310208282.X issued by the State Intellectual Property Office of People's Republic of China, dated Jun. 28, 2016, 3 pages.
English translation of Chinese Search Report regarding Chinese Application No. 201310208049.1 issued by the State Intellectual Property Office of People's Republic of China, 3 pages.
English translation of Japanese Office Action, Japanese Application No. 2013-112871, dated Mar. 21, 2017, 4 pages.

* cited by examiner

SURGICAL INSTRUMENTS AND METHODS OF SURGICALLY PREPARING A PATIENT'S TIBIA

This application is a continuation of U.S. patent application Ser. No. 15/445,109, now U.S. Pat. No. 9,962,173, which is a continuation of U.S. patent application Ser. No. 14/834,332, now U.S. Pat. No. 9,579,113, which is a continuation of U.S. patent application Ser. No. 13/485,444, now U.S. Pat. No. 9,113,915, which claimed priority under 35 U.S.C. § 119 to U.S. Patent Application No. 61/653,363, which was filed on May 30, 2012, each of which is incorporated herein by reference.

CROSS-REFERENCE

Cross reference is made to U.S. Pat. No. 9,028,501 entitled "TIBIAL ORTHOPAEDIC SURGICAL INSTRUMENTS AND METHOD OF USING SAME" and U.S. Pat. No. 9,095,356 entitled "TIBIAL TRIAL INSTRUMENTS AND METHOD OF USING SAME", each of which is assigned to the same assignee as the present application, and each of which is hereby incorporated by reference.

TECHNICAL FIELD

The present disclosure relates generally to orthopaedic instruments for use in the performance of an orthopaedic joint replacement procedure, and more particularly to orthopaedic surgical instruments for use in the performance of a revision knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, surgical reamers, drill guides, prosthetic trials, and other surgical instruments to prepare the patient's bones to receive the knee prosthesis.

SUMMARY

According to one aspect of the disclosure, an orthopaedic surgical instrument assembly is disclosed. The orthopaedic surgical instrument assembly includes an attachment device, an intramedullary orthopaedic surgical instrument, and a cutting block. The attachment device includes a housing having a longitudinal axis and a passageway defined therein that extends along the longitudinal axis. The attachment device also includes a pair of rails extending outwardly from the housing. Each rail has a longitudinal axis that extends orthogonal to the longitudinal axis of the housing. The attachment device also includes a mounting frame positioned on the pair of rails. The mounting frame is configured to slide relative to the housing along the pair of rails. The intramedullary orthopaedic surgical instrument includes a shaft positioned in the passageway of the housing. The cutting block is removably coupled to the mounting frame.

In some embodiments, the mounting frame may include a biasing element configured to inhibit movement of the mounting frame relative to the housing. In some embodiments, the biasing element may include a first cantilevered arm engaged with a first rail of the pair of rails and a second cantilevered arm engaged with a second rail of the pair of rails.

Additionally, in some embodiments, the cutting block may have a slot defined therein, and the mounting frame may include a flange that is moveable between a first position in which a tip of the flange is positioned in the slot such that the cutting block is secured to the mounting frame and a second position in which the tip of the flange is spaced apart from the slot such that the cutting block is removable from the mounting frame.

In some embodiments, the mounting frame may include a body having a pair of passageways defined therein and a locking mechanism. Each passageway may be sized to receive a rail of the pair of rails. The locking mechanism may include a flange, a control knob, and a central shaft connecting the flange to the control knob. The central shaft may be pivotally coupled to the body.

In some embodiments, the cutting block may have a pair of apertures defined in an upper surface thereof, and the mounting frame may have a pair of alignment pins that are received in the pair of apertures. In some embodiments, the attachment device may include a locking mechanism attached to the housing. The locking mechanism may be configured to secure the attachment device to the shaft of the intramedullary orthopaedic surgical instrument.

Additionally, in some embodiments, the locking mechanism may include a lever moveably coupled to the housing. The lever may be moveable between a first position in which a catch of the lever is engaged with the shaft of the intramedullary orthopaedic surgical instrument and a second position in which the catch is disengaged from the shaft.

In some embodiments, the intramedullary orthopaedic surgical instrument may include a surgical reamer and a stem trial. The surgical reamer may have a first end attached to the shaft and a second end positioned opposite the first end. The stem trial may be secured to the second end of the surgical reamer.

In some embodiments, the intramedullary orthopaedic surgical instrument may include a broach attached to the shaft. The broach may have a tapered outer surface and a plurality of cutting teeth extending outwardly from the tapered outer surface. In some embodiments, the broach may be removably coupled to the shaft. In some embodiments, the cutting block may have a plurality of cutting guides defined therein.

According to another aspect of the disclosure, an orthopaedic surgical instrument assembly is disclosed. The orthopaedic surgical instrument assembly includes a broach, a broach insert, an adaptor, an attachment device, and a cutting block. The broach includes a tapered outer surface, a plurality of cutting teeth formed on the tapered outer surface, and a slot defined in the upper end thereof. The broach insert is configured to be positioned in the slot of the broach. The broach insert includes a tapered outer surface, and a plurality of cutting teeth formed on the tapered outer surface. The adaptor includes a base configured to be positioned in the slot of the broach in place of the broach insert and a shaft extending from the base. The attachment device has a passageway defined therein sized to receive the shaft of the adaptor. The cutting block is configured to be coupled to the attachment device.

In some embodiments, the attachment device may include a housing having the passageway defined therein and a mounting frame movable relative to the housing. The mounting frame may be configured to be coupled to the cutting block.

In some embodiments, the cutting block may have a slot defined therein and a mounting frame. The mounting frame may include a locking tab that is moveable between a first position in which a tip of the locking tab is positioned in the slot such that the cutting block is secured to the mounting frame and a second position in which the tip of the locking tab is spaced apart from the slot such the cutting block is removable from the mounting frame.

In some embodiments, the mounting frame may include a locking mechanism. The locking mechanism may include a locking tab, a control knob, and a central shaft connecting the locking tab to the control knob. The shaft may have a longitudinal axis extending parallel to the longitudinal axis of the housing of the attachment device. In some embodiments, the mounting frame may be removably coupled to the housing.

According to another aspect of the disclosure, an orthopaedic surgical instrument assembly is disclosed. The orthopaedic surgical instrument assembly may include an attachment device, an intramedullary orthopaedic surgical instrument, and a cutting block. The attachment device includes a housing, a rail extending outwardly from the housing, and a mounting frame positioned on the rail. The mounting frame is configured to slide relative to the housing along the rail. The intramedullary orthopaedic surgical instrument is removably coupled to the housing. The cutting block is removably coupled to the mounting frame.

In some embodiments, the housing may have a passageway defined therein and an intramedullary orthopaedic surgical instrument. The intramedullary orthopaedic surgical instrument may include a shaft positioned in the passageway of the housing, a stem trial, and a surgical reamer connecting the shaft to the stem trial.

In some embodiments, the intramedullary orthopaedic surgical instrument may include a broach removably coupled to the housing. The broach may have a tapered outer surface, and a plurality of cutting teeth formed on the tapered outer surface.

According to another aspect of the disclosure, an orthopaedic surgical instrument assembly is disclosed. The orthopaedic surgical instrument assembly includes a tibial bearing trial, a tibial base trial, an intramedullary orthopaedic surgical instrument, and a fastener. The tibial bearing trial includes an articulation surface and a bottom surface opposite the articulation surface. The tibial base trial is adapted to be positioned on a surgically-prepared proximal end of a patient's tibia. The tibial base trial includes an upper surface engaged with the bottom surface of the tibial bearing trial. The intramedullary orthopaedic surgical instrument engages with a lower surface of the tibial base trial. The fastener is configured to pivot relative to the tibial base trial. The fastener includes a button head positioned in an aperture defined in the tibial bearing trial and a threaded shaft engaged with the intramedullary orthopaedic surgical instrument to removably couple the intramedullary orthopaedic surgical instrument to the tibial base trial.

In some embodiments, the intramedullary orthopaedic surgical instrument may include a broach engaged with the threaded shaft. The broach may have a tapered outer surface and a plurality of cutting teeth formed on the tapered outer surface.

In some embodiments, a second intramedullary orthopaedic surgical instrument may be configured to be engaged with the threaded shaft of the fastener in place of the broach. Additionally, in some embodiments, the second intramedullary orthopaedic surgical instrument may include a stem trial. In some embodiments, the tibial base trial may include a plate having an opening defined in the upper surface thereof and a platform positioned in the opening of the plate, and the fastener may extend through a bore defined in the platform.

In some embodiments, the orthopaedic surgical instrument assembly may include a base insert positioned in the opening defined in the plate of the tibial base trial. The base insert may include a lug positioned in the aperture defined in the tibial bearing trial. In some embodiments, the base insert may further include a frame having a circular opening defined therein and a pair of prongs extending outwardly from the frame, and the platform of the tibial base trial may be positioned in the circular opening.

In some embodiments, the base insert may further include a first lower arm and a second lower arm. The first lower arm may be attached to a first prong of the pair of prongs. The first lower arm may extend through an opening defined in the lower surface of the tibial base trial and may have a tapered outer surface and a plurality of cutting teeth formed on the tapered outer surface. The second lower arm may be attached to a second prong of the pair of prongs. The second lower arm may extend through an opening defined in the lower surface of the tibial base trial and may have a tapered outer surface, and a plurality of cutting teeth formed on the tapered outer surface.

In some embodiments, the intramedullary orthopaedic surgical instrument may include a slot, and the first lower arm and the second lower arm may be received in and may extend outwardly from the slot.

In some embodiments, the tibial bearing trial may include a tibial bearing surface trial and a shim. The tibial bearing surface trial may include the articulation surface. The shim may be secured to the tibial bearing surface trial. The shim may include the bottom surface.

According to another aspect, an orthopaedic surgical instrument assembly is disclosed. The orthopaedic surgical instrument assembly includes a tibial base trial, a fastener, an intramedullary orthopaedic surgical instrument, and a base insert. The tibial base trial is adapted to be positioned on a surgically-prepared proximal end of a patient's tibia. The fastener is configured to pivot relative to the tibial base trial. The fastener includes a button head, and a threaded shaft extending through the tibial base trial. The intramedullary orthopaedic surgical instrument is secured to the fastener. The base insert is positioned in an opening defined in the tibial base trial.

In some embodiments, an attachment tool may be configured to engage the base insert to attach and detach the base insert from the tibial base trial. In some embodiments, the base insert may have a pair of openings defined therein, and the attachment tool may include a pair of pegs configured to be received in the openings of the base insert. Each peg may include a spring configured to engage the base insert to secure the attachment tool to the base insert.

In some embodiments, the base insert may include a keel punch. The keel punch may include a first arm extending through a lower surface of the tibial base trial and a second arm extending through a lower surface of the tibial base trial. The first arm may extend through a lower surface of the tibial base trial. The first arm may include a tapered outer surface, and a plurality of cutting teeth formed on the tapered outer surface. The second arm may extend through a lower surface of the tibial base trial. The second arm may include a tapered outer surface, and a plurality of cutting teeth formed on the tapered outer surface.

In some embodiments, the intramedullary orthopaedic surgical instrument may include a slot, and portions of the first arm and the second arm may be received in and may extend outwardly from the slot.

In some embodiments, the intramedullary orthopaedic surgical instrument may include a broach engaged with the threaded shaft. The broach may include a tapered outer surface and a plurality of cutting teeth formed on the tapered outer surface.

In some embodiments, the base insert may include a frame, a pair of prongs extending outwardly from the frame, and a lug extending upwardly from the frame adjacent to the button head of the fastener.

In some embodiments, a tibial bearing trial may be coupled to the tibial base trial. The tibial bearing trial may include a tibial bearing surface trial having an articulation surface, and a shim having an aperture defined therein. The lug of the base insert and the button head of the fastener may be positioned in the aperture.

According to another aspect of the disclosure, an orthopaedic surgical instrument assembly is disclosed. The orthopaedic surgical instrument assembly includes a tibial base trial, a fastener, a first base insert, and a second base insert. The tibial base trial is adapted to be positioned on a surgically-prepared proximal end of a patient's tibia. The tibial base trial includes a plate having an opening defined in an upper surface thereof, and a platform positioned in the opening of the plate. The fastener is configured to pivot relative to the tibial base trial. The fastener includes a button head positioned above the upper surface and a threaded shaft extending through a bore defined in the platform of the tibial base trial. The first base insert is positioned in the opening defined in the tibial base trial including a frame positioned over the platform of the tibial base trial and a pair of prongs extending outwardly from the frame. The second base insert is configured to be positioned in the opening in place of the first base insert. The second base insert includes a first arm extending through a lower surface of the tibial base trial and a second arm extending through a lower surface of the tibial base trial. The first arm includes a tapered outer surface and a plurality of cutting teeth formed on the tapered outer surface. The second arm includes a tapered outer surface and a plurality of cutting teeth formed on the tapered outer surface.

In some embodiments, a plurality of intramedullary orthopaedic surgical instruments may be included. Each intramedullary orthopaedic surgical instrument may be configured to engage the fastener to secure the intramedullary orthopaedic surgical instrument to the tibial base trial.

According to another aspect of the disclosure, a method of surgically preparing a proximal end of a tibia is disclosed. The method of surgically preparing a proximal end of a tibia includes inserting an intramedullary orthopaedic surgical instrument into a medullary canal of the tibia, securing a housing of an attachment device to the intramedullary orthopaedic surgical instrument, sliding a mounting frame along a pair of rails toward the housing, attaching a cutting block to the mounting frame, resecting the proximal end of the tibia using the cutting guide to form a surgically-prepared surface, positioning a tibial base trial on the surgically-prepared surface, and inserting a keel punch through a slot defined in the tibial base trial and into the surgically-prepared surface of the tibia. The cutting block has a cutting guide defined therein.

In some embodiments, the method may include attaching a stem trial to an end of a surgical reamer to form the intramedullary orthopaedic surgical instrument. This may include inserting the intramedullary orthopaedic surgical instrument into the medullary canal, which may include reaming the proximal end of the tibia with the surgical reamer.

In some embodiments, the method may include removing the intramedullary orthopaedic surgical instrument from the medullary canal, attaching the stem trial to a modular stem, and securing the modular stem and the stem trial to the tibial base trial. This may include positioning the tibial base trial on the surgically-prepared surface, which may include inserting the modular stem and the stem trial into the medullary canal.

In some embodiments, the method may include inserting the keel punch through the slot defined in the tibial base trial and into the surgically-prepared surface of the tibia, which may include inserting a portion of the keel punch into a slot defined in the modular stem.

In some embodiments, the method may include inserting the intramedullary orthopaedic surgical instrument into the medullary canal of the tibia, which may include inserting a broach into the medullary canal to engage a plurality of cutting teeth with the tibia.

In some embodiments, the method may include withdrawing a broach insert from a slot defined in the broach and disengaging the cutting teeth of the broach insert from the tibia.

In some embodiments, the method may include attaching a mounting shaft to the broach, which may include securing the housing of the attachment device to the intramedullary orthopaedic surgical instrument, which may include sliding the housing along the mounting shaft.

In some embodiments, the method may include positioning the tibial base trial on the surgically-prepared surface, which may include engaging a fastener with the broach in the medullary canal to secure the tibial base trial to the broach. In some embodiments, the method may include inserting the keel punch through the slot defined in the tibial base trial and into the surgically-prepared surface of the tibia. In some embodiments, inserting the keel punch may include inserting a portion of the keel punch into the slot defined in the broach.

In some embodiments, the method may include attaching the cutting block to the mounting frame, which may include operating a control knob to move a locking tab of the mounting frame into engagement with the cutting block.

According to another aspect of the disclosure, a method of surgically preparing a proximal end of a tibia is disclosed. The method of surgically preparing a proximal end of a tibia includes inserting a broach into a medullary canal of the tibia, detaching a broach insert from the broach, securing an attachment device to the broach after detaching the broach insert, attaching a cutting block to the attachment device, resecting the proximal end of the tibia using the cutting guide to form a surgically-prepared surface, positioning a tibial base trial on the surgically-prepared surface, and securing the tibial base trial to the broach positioned in the medullary canal. The broach includes a tapered outer surface and a plurality of cutting teeth formed on the tapered outer surface. The cutting block has a cutting guide defined therein.

In some embodiments, the method may include inserting a base insert into an opening defined in the tibial base trial and positioning a tibial bearing trial over the lug of the base insert. The base insert may include a lug.

In some embodiments, the method may include removing the base insert from the tibial base trial and inserting a keel punch through a slot defined in the tibial base trial and into the surgically-prepared surface of the tibia. In some embodiments, the method may include securing the tibial base trial to the broach, which may include rotating a fastener to threadingly engage the broach.

Additionally, in some embodiments, the method may include securing an adaptor to the broach after detaching the broach insert. This may include securing the attachment device to the broach, which may include sliding the attachment device along a shaft of the adaptor. In some embodiments, the method may include securing the attachment device to the broach actuating a pair of levers to engage the levers with the shaft of the adaptor. In some embodiments, the method may include securing a stem trial to the broach before inserting the broach into the medullary canal.

According to another aspect of the disclosure, a method of surgically preparing a proximal end of a tibia is disclosed. The method of surgically preparing a proximal end of a tibia includes securing a stem trial to a surgical reamer, reaming a medullary canal of the tibia with the surgical reamer, securing an attachment device to a shaft of the surgical reamer while the surgical reamer and the stem trial are positioned in the medullary canal, attaching a cutting block to the attachment device, resecting the proximal end of the tibia using the cutting guide to form a surgically-prepared surface, removing the surgical reamer and the stem trial from the medullary canal, securing the modular stem and the stem trial to a tibial base trial, inserting the modular stem and the stem trial into the medullary canal, and positioning the tibial base trial on the surgically-prepared surface. The cutting block has a cutting guide defined therein.

In some embodiments, the method may include inserting a base insert into an opening defined in the tibial base trial and positioning a tibial bearing trial over the lug of the base insert. The base insert includes a lug.

In some embodiments, the method may include removing the base insert from the tibial base trial and inserting a keel punch through a slot defined in the tibial base trial and into the surgically-prepared surface of the tibia.

BRIEF DESCRIPTION OF THE DRAWINGS

The detailed description particularly refers to the following figures, in which.

DETAILED DESCRIPTION OF THE DRAWINGS

Figure 1:
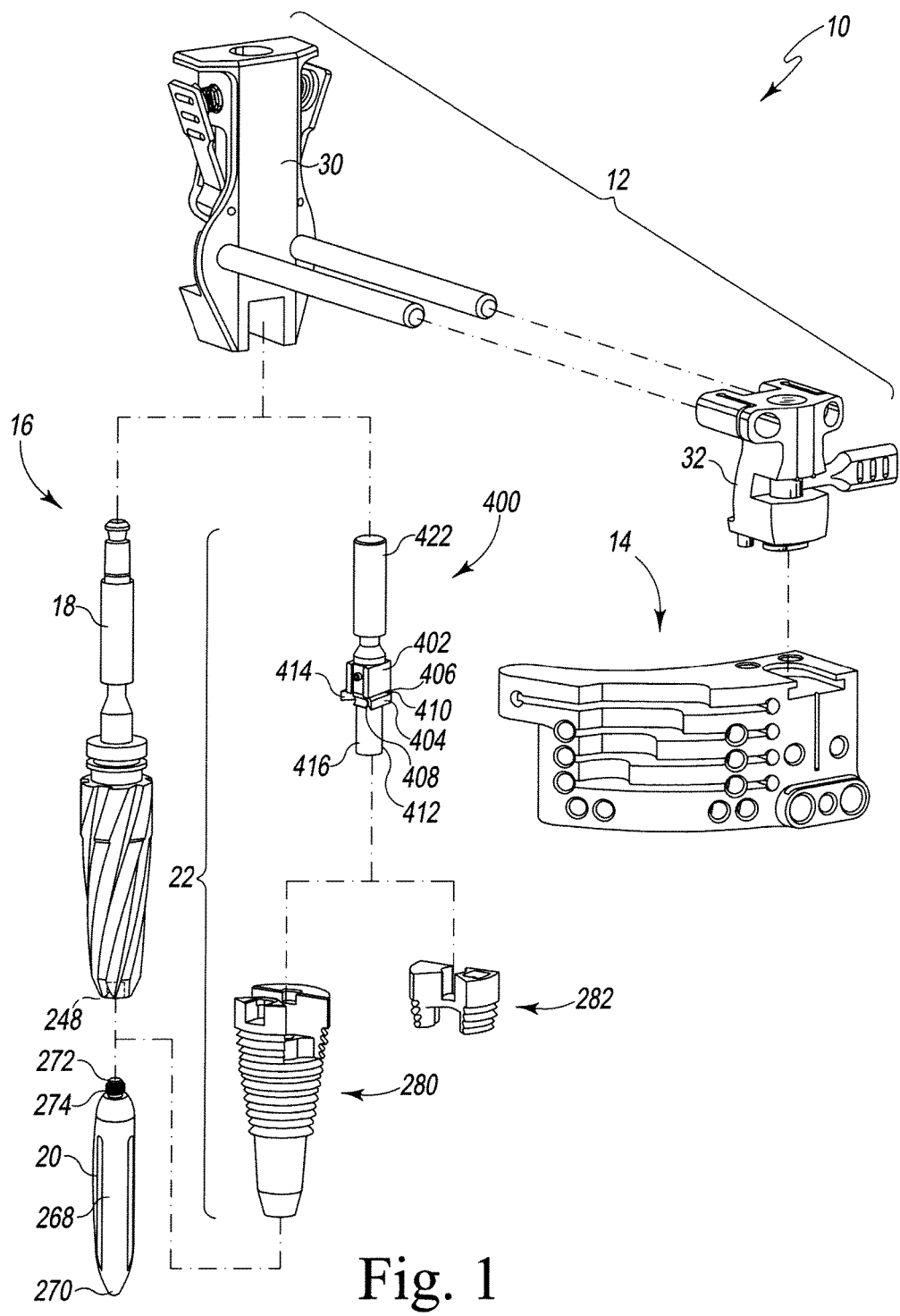
FIG. 1 is an exploded perspective view of a group of orthopaedic surgical instruments of an orthopaedic surgical instrument system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, a group of orthopaedic surgical instruments of an orthopaedic surgical instrument system 10 (hereinafter instrument system 10) is shown. What is meant herein by the term "orthopaedic surgical instrument" or "orthopaedic surgical instrument system" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic implants or prostheses that are surgically implanted in the body of the patient.

The system 10 includes an attachment device 12, a cutting block 14 configured to be secured to the attachment device 12, and a number of intramedullary orthopaedic surgical instruments 16 configured to be separately secured to the attachment device 12. What is meant herein by the term "intramedullary orthopaedic surgical instrument" is a surgical tool configured to be positioned in the medullary canal of the patient's tibia during the orthopaedic surgical procedure. Examples of intramedullary orthopaedic surgical instruments include stem trials, broaches, surgical reamers, and the like. As shown in FIG. 1, the intramedullary surgical instruments 16 include a surgical reamer 18, a stem trial 20, and a broach assembly 22. As described in greater detail below, the surgeon may use attachment device 12 and the intramedullary orthopaedic surgical instruments 16 position the cutting block 14 for use during the resection of the proximal end of a patient's tibia.

The attachment device 12 of the system 10 includes an attachment base 30 configured to be secured to an intramedullary orthopaedic instrument 16 and a mounting frame 32 configured to be moveably coupled to the base 30. The mounting frame 32 is also configured to be secured to the cutting block 14, as described in greater detail below. In the illustrative embodiment, the attachment base 30 and the mounting frame 32 are formed from a metallic material, such as, for example, stainless steel or cobalt chromium. It should be appreciated that in other embodiments the attachment base 30 or the mounting frame 32 may be formed from a polymeric material.

Figure 2:
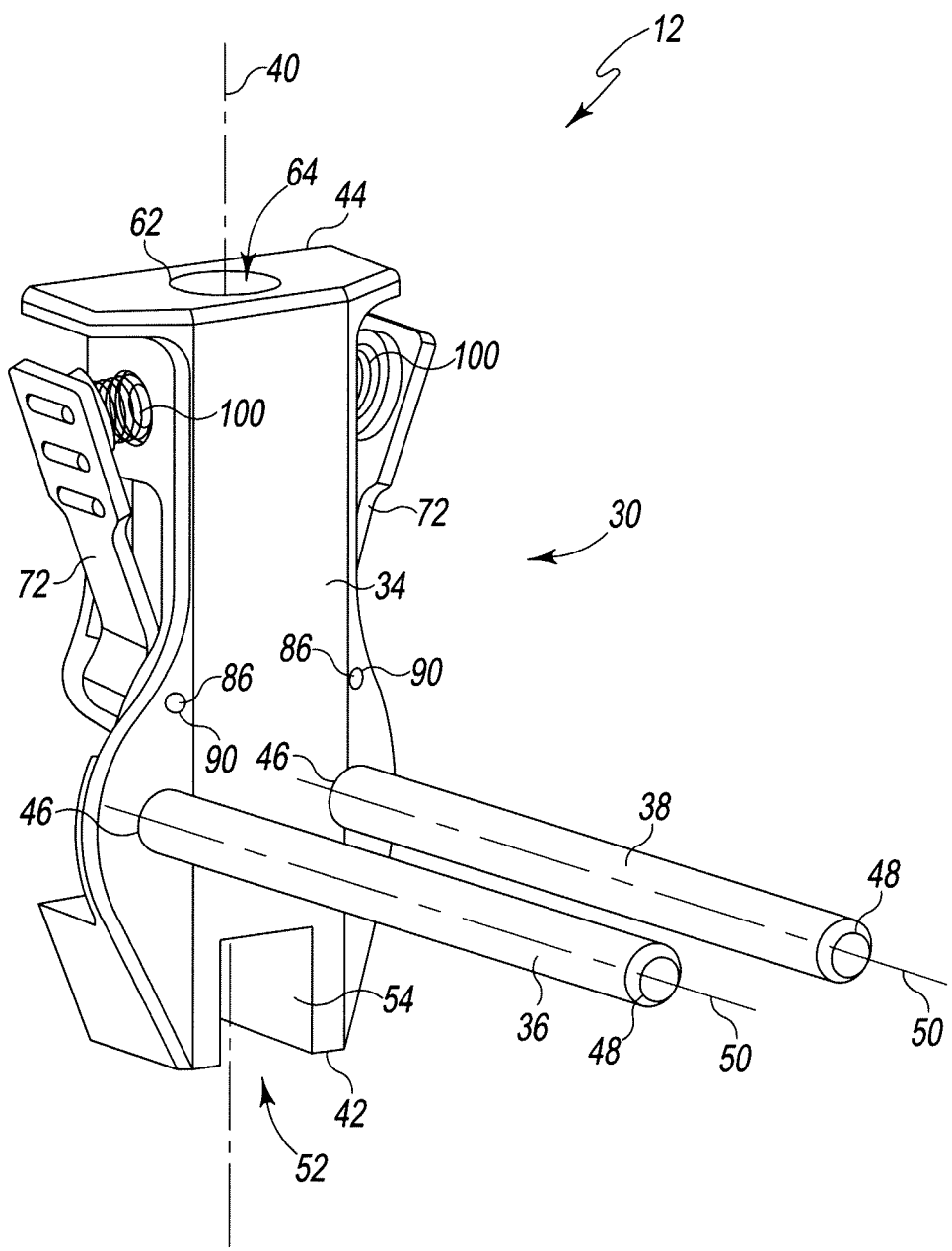
FIG. 2 is a perspective view of an attachment device of the instrument group of FIG. 1.
Figure 3:
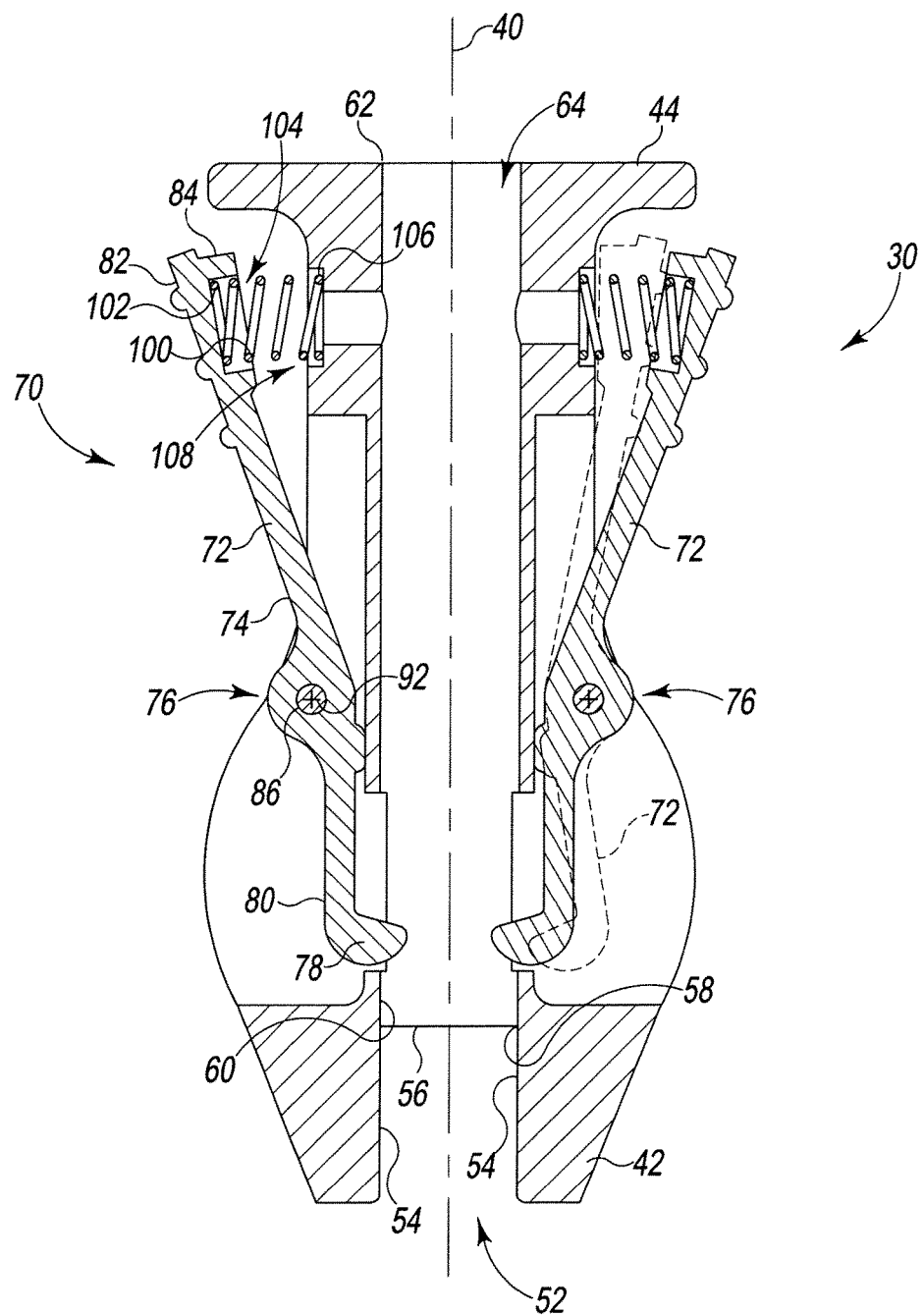
FIG. 3 is a cross-sectional elevation view of the attachment device of FIG. 2.

Referring now to FIGS. 2 and 3, the attachment base 30 includes a housing 34 and a pair of rails 36, 38 that extend outwardly from the housing 34. The housing 34 has a longitudinal axis 40 extending from a lower end 42 to an upper end 44. The rails 36, 38 extend parallel to each other, and each rail has an end 46 secured to the housing 34 and a tip 48. Each of the rails 36, 38 also has a longitudinal axis 50 that extends from the end 46 to the tip 48. In the illustrative embodiment, the longitudinal axes 50 of the rails 36, 38 extend orthogonal to the longitudinal axis 40 of the housing 34. As shown in FIG. 2, each of the rails 36, 38 is circular in cross-section, but it should be appreciated that in other embodiments each rail may have a square, rectangular, or other cross-sectional shape. It should also be appreciated that in other embodiments the attachment base 30 may include only a single rail. In other embodiments, the rails may not extend orthogonal relative to the longitudinal axis 40 of the housing 34.

The housing 34 of the attachment base 30 has a channel 52 defined in the lower end 42 thereof. The channel 52 is defined by a pair of side walls 54 and a substantially planar surface 56 extending between the side walls 54. As shown in FIG. 3, the planar surface 56 has an opening 58 defined therein, and an inner wall 60 extends upwardly from the opening 58 to an opening 62 defined in the upper end 44 of the housing 34. In that way, the inner wall 60 defines a passageway 64 through the housing 34 that extends along the longitudinal axis 40. As described in greater detail below, the passageway 64 is sized to receive a shaft of an intramedullary orthopaedic surgical instrument 16.

The attachment base 30 also includes a locking mechanism 70 configured to secure the attachment device 12 to the intramedullary orthopaedic surgical instrument 16. In the illustrative embodiment, the locking mechanism 70 includes a pair of levers 72 pivotally coupled to the housing 34. As shown in FIG. 3, each lever 72 includes an arm 74 coupled to the housing 34 via a joint 76. The lever 72 also includes a catch 78 extending from one end 80 of the arm 74 and a handle 82 formed on the opposite end 84.

The joint 76 includes a pin 86 that extends through the arm 74 and is received in apertures 90 (see FIG. 2) defined in the housing 34. Each lever 72 is configured to pivot about an axis 92 defined by the pin 86 between an engaged position (shown in solid line in FIG. 3) and a disengaged position (shown in broken line in FIG. 3). In the engaged position, the catch 78 extends through an opening 94 defined in the housing 34 into the passageway 64. As such, the catch 78 engages an instrument 16 when the instrument is positioned in the passageway 64. In the disengaged position, the catch 78 is removed from the passageway 64 such that the catch 78 is disengaged from the instrument 16.

The locking mechanism 70 of the attachment device 12 also includes biasing elements 100 configured to bias each lever 72 into the engaged position. In the illustrative embodiment, each biasing element is a spring 100 having an end 102 positioned in an aperture 104 defined in the end 84 of the arm 74. The opposite end 106 of each spring 100 is positioned in an aperture 108 defined in the housing 34.

Figure 4:
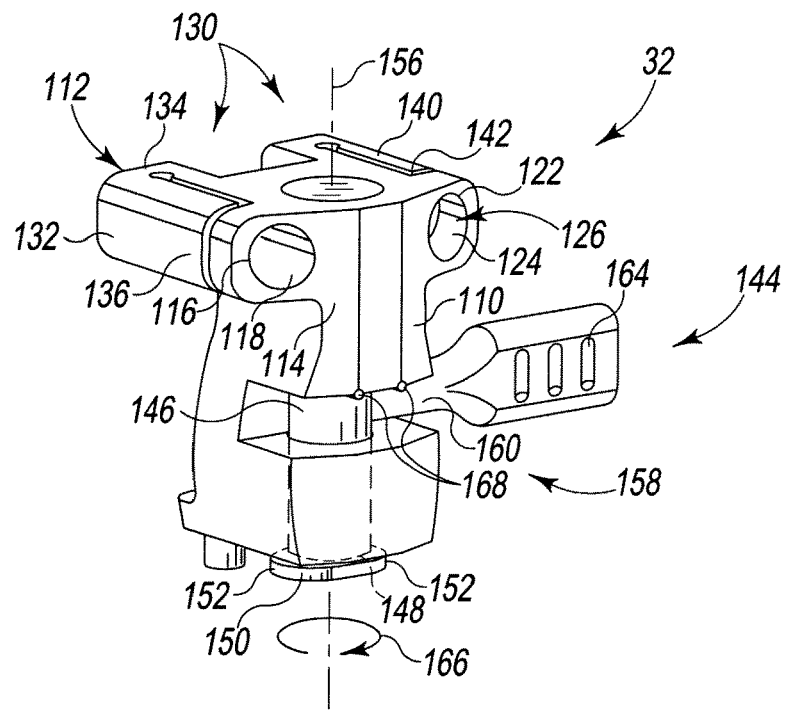
FIG. 4 is a perspective view of a mounting frame of the attachment device of FIG. 2.
Figure 5:
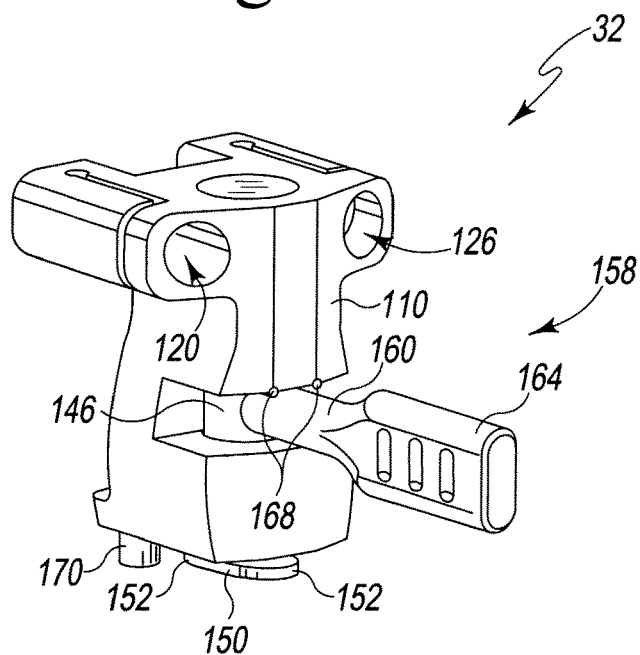
FIG. 5 is an elevation view of the mounting frame of FIG. 4.

As described above, the attachment device 12 of the system 10 also includes a mounting frame 32 configured to be movably coupled to the attachment base 30. Referring now to FIGS. 4 and 5, the mounting frame 32 includes a body 110 having a rear surface 112 that confronts the housing 34 and a front surface 114 positioned opposite the rear surface 112. The front surface 114 has an opening 116 defined therein, and a cylindrical inner wall 118 extends inwardly from the opening 116 to define a passageway 120 extending through the body 110. The passageway 120 is sized to receive the rail 36 of the attachment base 30.

The front surface 114 of the body 110 has another opening 122 defined therein. A cylindrical inner wall 124 extends inwardly from the opening 122 to define another passageway 126 through the body 110. As shown in FIG. 4, the passageway 126 extends parallel to the passageway 120, and the passageway 126 is sized to receive the other rail 38 of the attachment base 30. When the mounting frame 32 is coupled to the attachment base 30, the rails 36, 38 are positioned in the passageways 120, 126, and the mounting frame 32 is configured to slide along the rails 36, 38 relative to the housing 34 of the attachment base 30.

The mounting frame 32 of the attachment device 12 also includes a retention mechanism 130 configured to inhibit movement of the mounting frame 32 relative to the housing 34. In the illustrative embodiment, the retention mechanism 130 includes a cantilevered arm 132 secured at one end 134 to the body 110 of the mounting frame 32. As shown in FIG. 4, the cantilevered arm 132 includes a free end 136 configured to engage rail 36 when the mounting frame 32 is coupled to the attachment base 30. The retention mechanism 130 also includes a cantilevered arm 140 that has a free end 142 configured to engage the other rail 38 when the mounting frame 32 is coupled to the attachment base 30. The free ends 136, 142 of the arms 132, 140 exert a bias on the rails 36, 38 that inhibits movement of the mounting frame 32.

In use, when a surgeon or other user applies sufficient force in a direction, for example, toward the attachment base 30, the bias exerted by the cantilevered arms 132, 140 is overcome such that the mounting frame 32 may be advanced along the rails 36, 38 toward the attachment base 30. When the surgeon no longer applies the force, the bias exerted by the arms 132, 140 prevents further movement of the mounting frame 32.

In other embodiments, the retention mechanism may include a clamp configured to be selectively engaged with the rails. In still other embodiments, the retention mechanism may include a fastener, latch, or other mechanism to prevent relative movement between the mounting frame 32 and the attachment base 30. Additionally, in the illustrative embodiment, the mounting frame 32 is detachable from the attachment base 30. It should be appreciated that in other embodiments the attachment device 12 may be configured such the mounting frame 32 is non-removable from the attachment base 30.

As described above, the mounting frame 32 of the attachment device 12 is configured to be secured to the cutting block 14. As shown in FIGS. 4 and 5, the mounting frame 32 includes a locking mechanism 144 configured to selectively engage the cutting block 14. In the illustrative embodiment, the locking mechanism 144 includes a central shaft 146 pivotally coupled to the body 110 of the mounting frame 32. The central shaft 146 has a lower end 148 that extends downwardly from the body 110. A plug 150 is formed on the lower end 148 of the central shaft 146, and the plug 150 includes a pair of flanges 152 that extend outwardly from the central shaft 146. As described in greater detail below, the flanges 152 are configured to be received in a channel 154 defined in the cutting block 14 to selectively secure the cutting block 14 to the mounting frame 32.

As shown in FIG. 4, the central shaft 146 of the locking mechanism 144 has a longitudinal axis 156. The locking mechanism 144 also includes a control knob 158 operable to rotate the central shaft 146 (and hence plug 150) about the axis 156. In the illustrative embodiment, the control knob 158 includes an arm 160 secured to the central shaft 146. The arm 160 extends outwardly from the central shaft 146 through a slot 162 defined in the front surface 114 of the body 110. The arm 160 includes a grip 164 that is spaced apart from the body 110, and the grip 164 may be grasped by the user to operate the control knob 158.

The control knob 158 is operable to rotate the plug 150 in the direction indicated by arrow 166 between an engaged position (see FIG. 4) and a disengaged position (see FIG. 5). In the engaged position, the flanges 152 are received in the channel 154 defined in the cutting block 14, thereby securing the cutting block 14 to the mounting frame 32. In the disengaged position, the flanges 152 are removed from the channel 154, thereby releasing the block 14. As shown in FIG. 5, the arm 160 of the control knob 158 is positioned between a pair of lips 168 formed on the body 110 when the plug 150 is in the disengaged position.

In other embodiments, the control knob may have a handle or grip secured to the upper end of the central shaft 146. In still other embodiments, the locking mechanism 144 may include a lever pivotally coupled the mounting frame that is selectively engaged with and disengaged with the cutting block. In other embodiments, the locking mechanism 144 may include any combination of latches or other fasteners to secure the cutting block 14 to the attachment device 12.

As shown in FIGS. 4 and 5, the mounting frame 32 also includes a pair of alignment pins 170 extending downwardly from the body 110. Each alignment pin 170 is sized and shaped to be received in an aperture 172 defined in the cutting block 14. In the illustrative embodiment, each pin 170 has a circular cross section. It should be appreciated that in other embodiments each pin may have a square, rectangular, or other cross-sectional shape.

Figure 6:
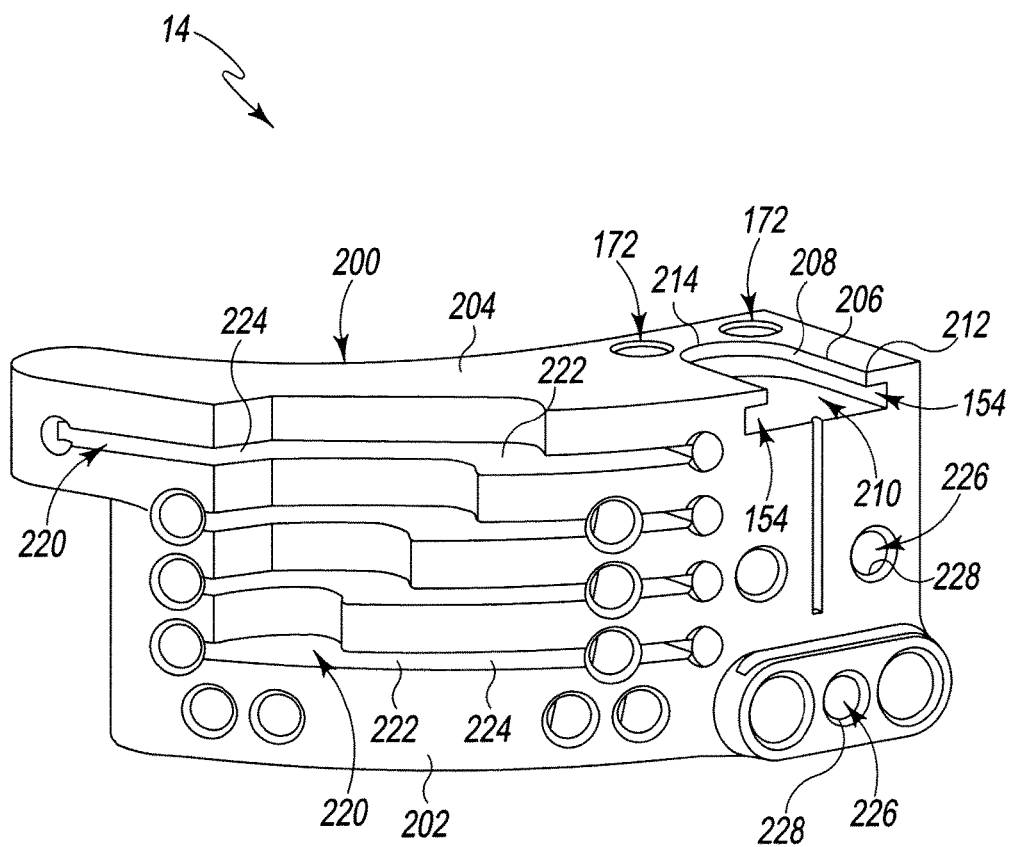
FIG. 6 is a perspective view of a cutting block of the instrument group of FIG. 1.

Referring now to FIG. 6, the system 10 includes a cutting block 14. The cutting block 14 includes a posterior side wall 200 that is configured to confront the anterior side of the patient's tibia, as described in greater detail below. The cutting block 14 also includes an anterior side wall 202 that is positioned opposite the posterior side wall 200. An upper surface 204 connects the side walls 200, 202. In the illustrative embodiment, the cutting block 14 is formed from a metallic material, such as, for example, stainless steel or cobalt chromium.

An opening 206 is defined in the upper surface 204, and an inner wall 208 extends downwardly from the opening 206 to define a slot 210 in the cutting block 14. As shown in FIG. 6, the slot 210 has an open end 212 defined in the anterior side wall 202, and a closed end 214 positioned between the side walls 200, 202. The inner wall 208 has a channel 154 defined therein. As described above, the channel 154 is sized to receive the flanges 152 of the locking mechanism 144 to secure the cutting block 14 to the attachment device 12.

The cutting block 14 also includes a pair of apertures 172 positioned on each side of the slot 210. As described above, the apertures 172 are sized to receive the alignment pins 170 of the mounting frame 32.

The cutting block 14 includes a number of cutting guides 220 that may be used during an orthopaedic surgical procedure to resect a portion of the patient's bone. Each cutting guide 220 includes an elongated slot sized to receive a cutting saw blade of a surgical saw or other surgical device. In the illustrative embodiment, the cutting block 14 has four cutting guides 220 extending through the side walls 200, 202. Each cutting guide 220 includes a planar surface 222 that defines a resection plane 224.

The resection planes 224 extend through the patient's tibia when the cutting block 14 is secured to the attachment device 12 on the tibia. In that way, the cutting guides 220 may be used by the orthopaedic surgeon during the resection of the patient's tibia. In the illustrative embodiment, the cutting guides 220 (hence the resection planes 224) are spaced part from each other by about five millimeters. As such, the surgeon may select the particular cutting guide 220 corresponding to the amount of bone to be removed. In other embodiments, the cutting block 14 may include any number of cutting guides 220, which may be spaced apart by an amount greater than or less than five millimeters.

As shown in FIG. 6, the cutting block 14 includes a plurality of fastener guides 226. Each guide 226 includes a bore 228 sized to receive fasteners such as, for example, fixation pins 230 (see FIG. 24), which may be utilized to secure the cutting block 14 to the patient's tibia. It should be appreciated that in other embodiments the cutting block 14 may include additional fastener guides 226 or other fastening elements to secure the cutting block to the patient's tibia. The angle of each fastener guide 226 may also vary to provide additional security with the bone.

Figure 7:
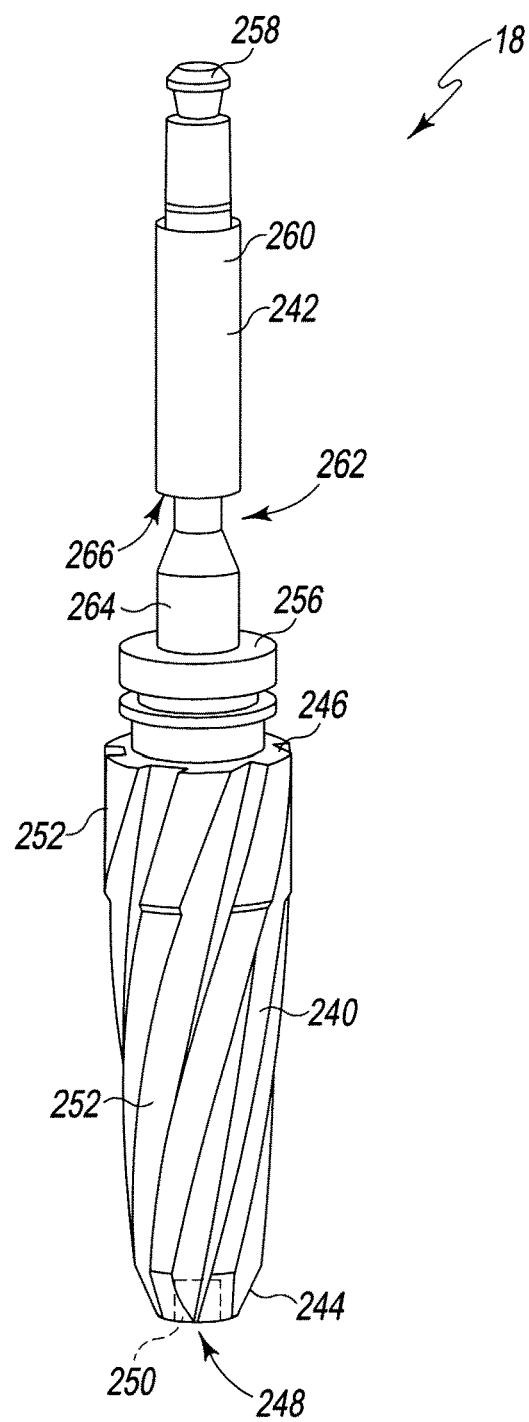
FIG. 7 is an elevation view of a surgical reamer of the instrument group of FIG. 1.
Figures 8, 9:
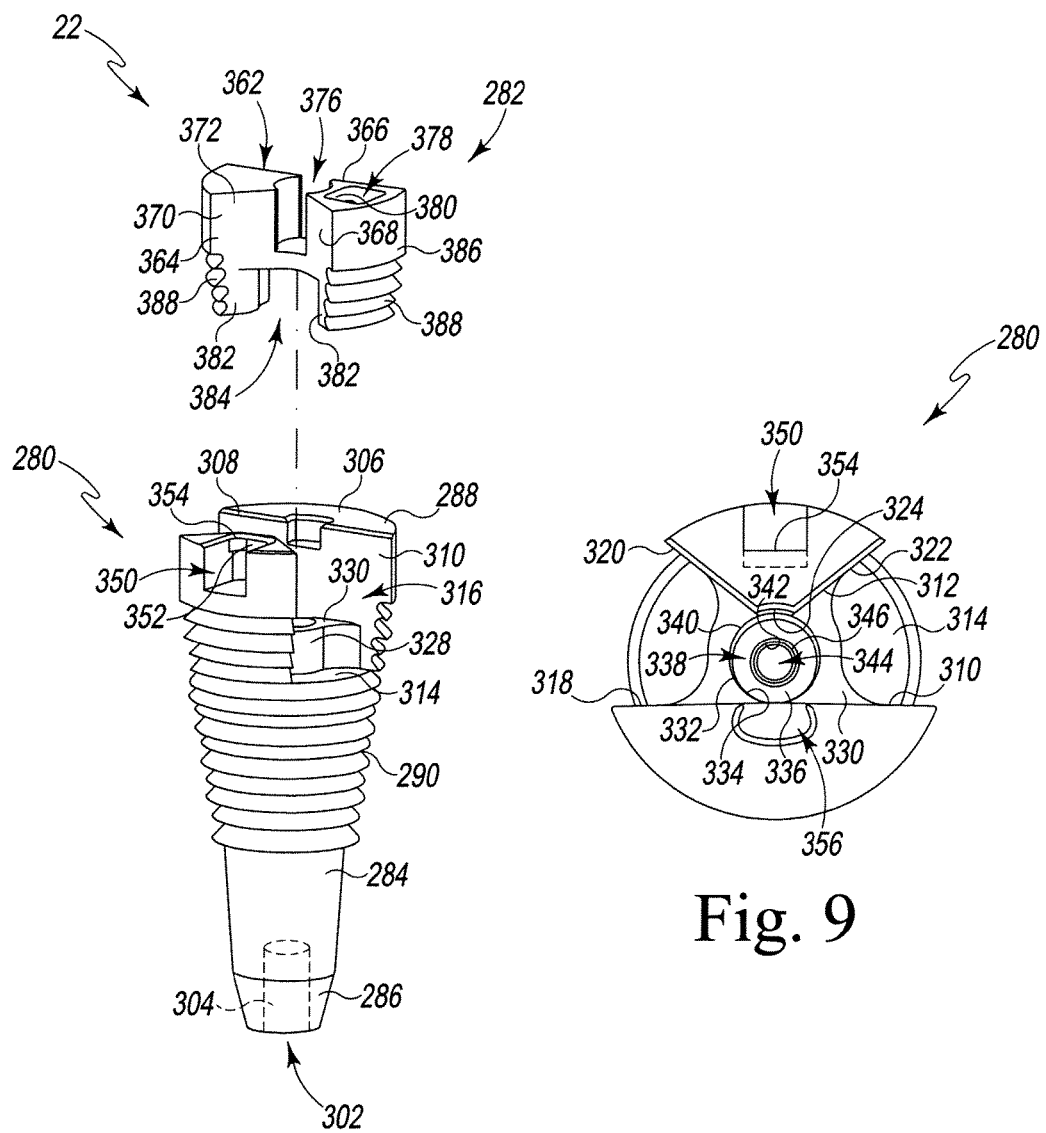
FIG. 8 is a perspective view of a broach and a broach insert of the instrument group of FIG. 1.
FIG. 9 is a plan view of the broach of FIG. 8.
Figure 10:
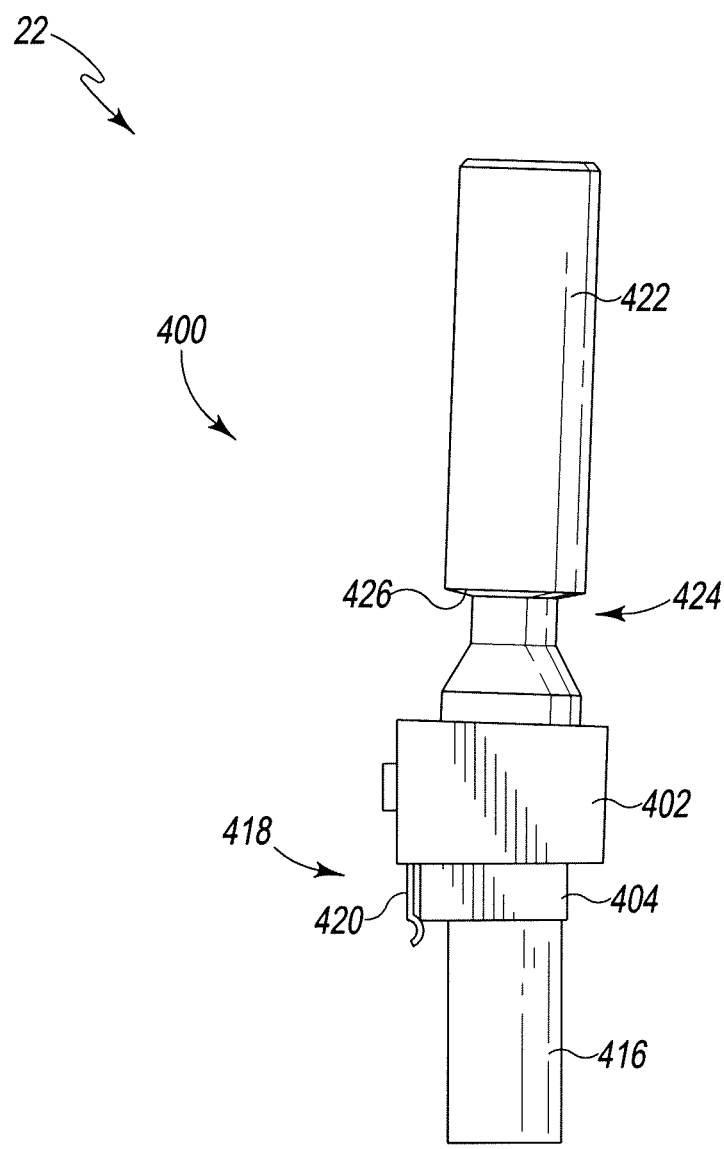
FIG. 10 is an elevation view of an adaptor of the instrument group of FIG. 1.

As described above, the system 10 also includes a number of intramedullary orthopaedic surgical instruments 16, including a surgical reamer 18 (see FIG. 7), a stem trial 20 (see FIG. 1), and a broach assembly 22 (see FIGS. 8-10). In the illustrative embodiment, each of the intramedullary orthopaedic surgical instruments 16 is formed from a metallic material, such as, for example, stainless steel or cobalt chromium. Referring now to FIG. 7, the surgical reamer 18 includes a cutting head 240 and an elongated shaft or shank 242 secured to the cutting head 240. In the illustrative embodiment, the cutting head 240 is conical and extends from a tip 244 to an upper end 246. The tip 244 of the cutting head 240 has an aperture 248 defined therein. An inner wall 250 defines the aperture 248, and the inner wall 250 has a plurality of internal threads (not shown) formed thereon.

The cutting head 240 of the reamer 18 includes a plurality of cutting flutes 252 extending between the tip 244 and the end 246. When the surgical reamer 18 is positioned in the medullary canal 254 (see FIG. 23) of the patient's tibia and rotated, the cutting flutes 252 of the cutting head 240 ream or otherwise cut the bone tissue of the tibia. It should be appreciated that other reamers having cutting heads of different configurations may be provided. For example, the outer diameter of the cutting head may vary to produce reamed canals sized to accommodate prosthetic components of different sizes. Additionally, the length of the cutting head may vary to change the depth of the reamed canal.

The shank 242 of the surgical reamer 18 has a platform 256 attached to the cutting head 240 and an upper end 258 that fits into the chuck of a rotary power tool or a manual handle. A cylindrical body 260 is positioned between the upper end 258 and the platform 256. The cylindrical body 260 is sized to be positioned in the passageway 64 defined in the attachment base 30. A recess 262 is defined in the cylindrical body 260 and is sized to receive the catches 78 of the levers 72 of the attachment base 30.

When the attachment device 12 is secured to the surgical reamer 18, the lower end 42 of the attachment base 30 is seated on the platform 256 of the shank 242. As shown in FIG. 7, the cylindrical body 260 of the shank 242 has a lower end 264 that extends upwardly from the platform 256. The lower end 264 of the body 260 is received in the channel 52 defined in the attachment base 30 when the attachment device 12 is seated on the shank 242. The catches 78 of the levers 72 are positioned in the recess 262 of the cylindrical body 26. In the illustrative embodiment, the cylindrical body 260 has a stop surface 266 that is configured to engage the catches 78 to prevent the attachment device 12 from being removed from the reamer 18.

Returning to FIG. 1, the system 10 also includes a stem trial 20. It should be appreciated that other stem trials having different configurations may be provided. For example, the outer diameter and/or length of the stem trial may vary to trial prosthetic components of different sizes. In the illustrative embodiment, the stem trial 20 has a body 268 that extends from a tip 270 to an upper end 272. The upper end 272 has a plurality of external threads 274 that correspond to the internal threads surrounding the aperture 248 of the shank 242. The upper end 272 of the stem trial 20 is sized to be received in the aperture 248 to engage the internal threads with the external threads 274 and thereby secure the stem trial 20 to the surgical reamer 18. It should be appreciated that in other embodiments the stem trial 20 may be engaged with surgical reamer 18 without being secured thereto.

As described above, the intramedullary orthopaedic surgical instruments 16 of the system 10 include a broach assembly 22 configured to be positioned in the medullary canal 254 of the patient's tibia. Referring now to FIGS. 8 and 9, the broach assembly 22 includes a broach 280 and a broach insert 282 configured to be removably coupled to the broach 280. The broach 280 includes an outer surface 284 extending from a tip 286 to an upper end 288. The outer surface 284 is tapered, with the diameter of the broach 280 decreasing from the upper end 288 to the tip 286.

A plurality of cutting teeth 290 are formed on the outer surface 284 between the tip 286 and the upper end 288. As described in greater detail below, the cutting teeth 290 are configured to engage the bone surrounding the medullary canal 254 when the broach 280 is inserted therein. It should be appreciated that other broaches having different configurations may be provided. For example, the outer diameter and/or length of the broach may vary to produce different sized canals to accommodate prosthetic components of different sizes.

As shown in FIG. 8, the tip 286 of the broach 280 has an aperture 302 defined therein. An inner wall 304 defines the aperture 302, and the inner wall 304 has a plurality of internal threads (not shown) formed thereon. The aperture 302 is sized to receive the upper end 272 of the stem trial 20 such that the internal threads engage with the external threads 274 and thereby secure the stem trial 20 to the broach 280.

The broach 280 includes a substantially planar top surface 306 at the upper end 288 thereof. An opening 308 is defined in the top surface 306, and the broach 280 has inner walls 310, 312 that extend downwardly from the top surface 306. The inner walls 310, 312 cooperate with a bottom wall 314 to define a slot 316 in the broach 280. As shown in FIGS. 8 and 9, the slot 316 extends through the outer surface 284 of the broach 280.

The inner wall 310 of the broach 280 has a planar surface 318 that extends inwardly from the outer surface 284. The other inner wall 312 has a pair of planar surfaces 320, 322 that extend inwardly from the outer surface 284. As shown in FIG. 9, the planar surface 322 extends at an oblique angle α relative to the planar surface 320. An arcuate surface 324 connects the planar surface 322 to the planar surface 320.

A platform 328 extending upwardly from the bottom wall 314 is positioned in the slot 316. The platform 328 has a top surface 330 and an opening 332 defined in the top surface 330. A cylindrical wall 334 extends inwardly from the opening 332 to a lower surface 336. The lower surface 336 and the cylindrical wall 334 cooperate to define a bore 338 in the platform 328. As shown in FIG. 9, the lower surface 336 has another opening 340 defined therein, and another cylindrical wall 342 extends inwardly from the opening 340. The cylindrical wall 342 defines an aperture 344 within the broach 280 and has a plurality of internal threads 346 formed thereon.

The upper end 288 of the broach 280 has another slot 350 defined therein. The slot 350 extends inwardly from the outer surface 284 through the top surface 306 to a side wall 352. A flange 354 extends from the side wall 352 into the slot 350. Another slot 356 is formed in the upper end 288. As shown in FIG. 9, the slot 356 opens into the slot 316.

As described above, the broach assembly 22 also includes a broach insert 282. As shown in FIG. 8, the broach insert 282 is sized and shaped to be received in the slot 316 defined in the broach 280. The broach insert 282 has a pair of side walls 362, 364 that confront the inner walls 310, 312, respectively, of the broach 280 when the broach insert 282 is positioned in the slot 316. The side wall 362 of the broach insert 282 has a planar surface 366 that engages the planar surface 318 of the broach 280 when the broach insert 282 is coupled to the broach 280. The other side wall 362 has a pair of planar surfaces 368, 370 that correspond to and engage the planar surfaces 320, 322 of the broach 280 when the broach insert 282 is coupled to the broach 280.

The broach insert 282 includes a main body 372 that has an upper surface 374. As shown in FIG. 8, the upper surface 374 has a central slot 376 defined therein. Another slot 378 is defined in the upper surface 374 adjacent to the central slot 376. A flange 380 extends into the slot 378.

The broach insert 282 includes a pair of legs 382 that extend downwardly from the main body 372. An opening 384 is defined between the legs 382. As shown in FIG. 8, the opening 384 is sized to receive the platform 328 of the broach 280. When the broach insert 282 is receive in the slot 316 of the broach 280, the legs 382 engage the bottom wall 314 and are positioned on each side of the platform 328.

The broach insert 282, like the broach 280, has an outer surface 386 that is tapered. The outer surface 386 has a plurality of cutting teeth 388 formed on the outer surface 284. As described in greater detail below, the cutting teeth 388 are configured to engage the bone surrounding the medullary canal 254 when the broach insert 282 is inserted therein.

Returning to FIG. 1, the broach assembly 22 also includes an adaptor 400 configured to connect the broach 280 to the attachment device 12. The adaptor 400 includes a base 402 and a plug 404 secured to the base 402. The adaptor 400 is configured to be coupled to the broach 280, and the plug 404 is configured to be positioned in the slot 316 when the adaptor 400 is coupled to the broach 280. The plug 404 includes a pair of side walls 406, 408 that confront the inner walls 310, 312, respectively, of the broach 280 when the plug 404 is positioned in the slot 316. The side wall 406 of the plug 404 has a planar surface 410 that engages the planar surface 318 of the broach 280 when the adaptor 400 is coupled to the broach 280. The other side wall 408 has a pair of planar surfaces 412, 414 that correspond to and engage the planar surfaces 320, 322 of the broach 280 when the adaptor 400 is coupled to the broach 280.

As shown in FIG. 10, the adaptor 400 includes a post 416 extending downwardly from the plug 404. The post 416 is configured to be received in the bore 338 defined in the platform 328 of the broach 280 when the adaptor 400 is secured to the broach 280. The adaptor 400 includes a biasing element 418 configured to retain the adaptor 400 on the broach 280. In the illustrative embodiment, the biasing element 418 is a cantilevered spring 420 configured to engage the inner wall 310 of the broach 280 when the adaptor 400 is positioned in the slot 316. It should be appreciated that in other embodiments the adaptor 400 may include latches, pins, or other fasteners to secure to the adaptor 400 to the broach 280.

Another shaft 422 extends upwardly from the base 402. The shaft 422 is sized to be positioned in the passageway 64 defined in the attachment base 30. A recess 424 is defined in the shaft 422 and is sized to receive the catches 78 of the levers 72 of the attachment device 12. When the attachment device 12 is secured to the adaptor 400, the lower end 42 of the attachment base 30 is seated on the plug 404 of the adaptor 400. The base 402 of the adaptor 400 is received in the channel 52 defined in the attachment base 30 when the attachment device 12 is seated on the adaptor 400. The catches 78 of the levers 72 are positioned in the recess 424 of the shaft 422. In the illustrative embodiment, the shaft 422 has a stop surface 426 that is configured to engage the catches 78 to prevent the attachment device 12 from being removed from the adaptor 400.

Figure 11:
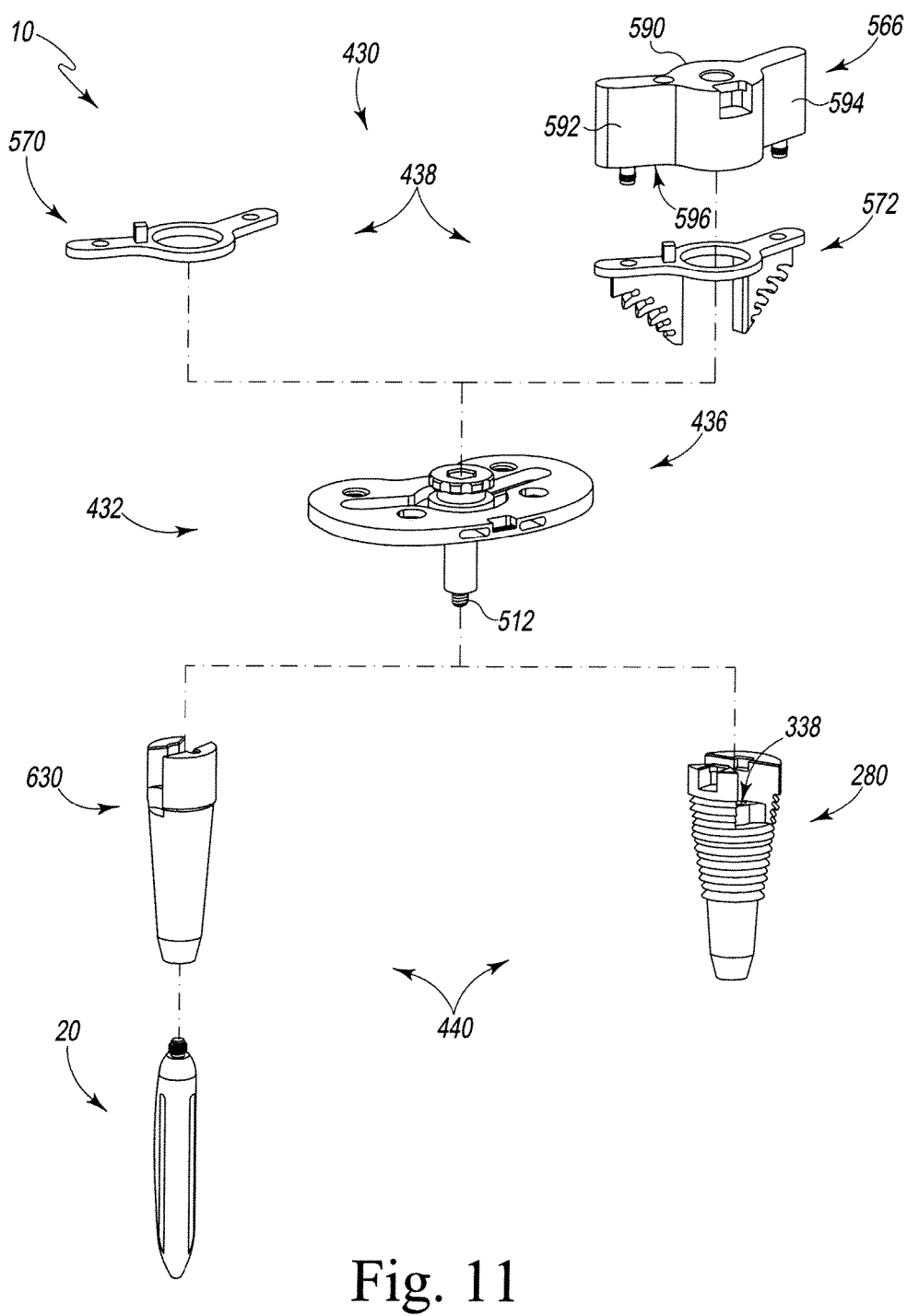
FIG. 11 is an exploded perspective view of another group of orthopaedic surgical instruments of the orthopaedic surgical instrument system.

Referring now to FIGS. 11-20, the orthopaedic surgical instrument system 10 includes a tibial tray trial assembly 432 (see FIG. 11) and a number of tibial bearing trial assemblies 434 (see FIG. 20) that may be used to size and select the prosthetic components of a knee prosthesis that will replace the patient's natural joint. As shown in FIG. 11, the tibial tray trial assembly 432 includes a tibial base trial 436, a number of base inserts 438, and a number of intramedullary surgical instruments 440. In the illustrative embodiment, the tibial tray trial assembly 432 is formed from a metallic material, such as, for example, stainless steel or cobalt chromium.

Figure 12:
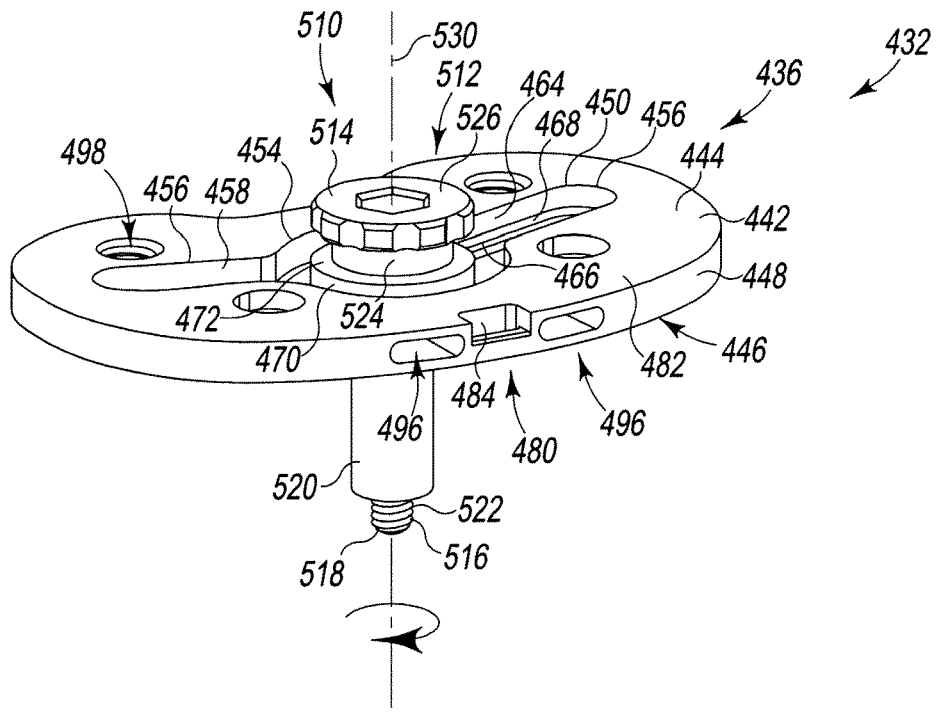
FIG. 12 is a perspective view of a tibial base trial and a fastener of the instrument group of FIG. 11.

Referring now to FIG. 12, the base trial 436 includes a plate 442 having an upper surface 444, a lower surface 446, and an outer side wall 448 extending between the surfaces 444, 446. The plate 442 has a plate opening 450 defined in the upper surface 452. The plate opening 450 has a central opening 454 and a pair of elongated openings 456 extending outwardly therefrom. An inner wall 458 extends downwardly from the opening 450 to define a passageway 460 and a passageway 462 through the plate 442. As will be described in greater detail below, the configuration of the passageways 460, 462 permits the advancement of a keel punch and various other instruments into the proximal end of the patient's tibia. It should be appreciated that the tibial base trial 436 may be formed in a number of different sizes to accommodate tibias of various sizes.

The inner wall 458 includes an upper wall 464 and a lower wall 466 offset or otherwise spaced inwardly from the upper wall 464. The upper wall 464 and the lower wall 466 cooperate to define a shelf surface 468 therebetween. A platform 470 is positioned in the central opening 454 of the plate 442. As shown in FIG. 12, the platform 470 extends upwardly from the shelf surface 468 and has a top surface 472 that is co-planar with the upper surface 444 of the plate 442.

In the illustrative embodiment, the plate 442 also includes a lever-receiving notch 480 that is defined in an anterior aspect 482 thereof. The notch 480 includes a channel 484 that is defined in the upper surface 444 and extends posteriorly from the outer side wall 448. An oblong-shaped slot 490 is defined in the posterior end 492 of the channel 484. The slot 494 extends downwardly through the lower surface 446 of the plate 442. As shown in FIG. 12, a pair of oblong-shaped apertures 496 are defined in the side wall 448, one on each side of the notch 480. The notch 480 and the apertures 496 are configured to receive a lever and a pair of pins, respectively, associated with an alignment handle.

Figure 13:
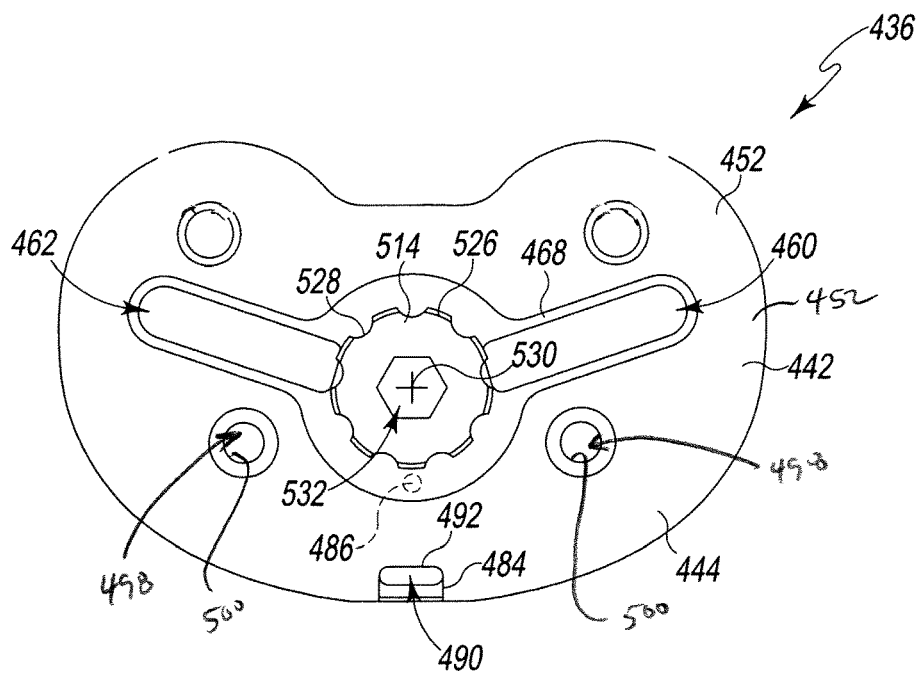
FIG. 13 is a plan view of the tibial base trial of FIG. 12.

As shown in FIG. 13, a pin 486 extends downwardly from the lower surface 446 of the plate 442. As described in greater detail below, the pin 486 is sized to be received in the slot 356 defined in the broach 280. The plate 442 also includes a number of fastener guides 498 that are defined in the anterior aspect 482 thereof. Each fastener guide 498 includes a bore 500 configured to receive a fastener such as a fixation pin, which may be utilized to secure the base trial 436 to the proximal end of the patient's tibia.

As shown in FIG. 12, the tibial base trial assembly 432 includes a locking mechanism 510 configured to secure the tibial base trial 436 to one of the intramedullary orthopaedic surgical instruments 440. In the illustrative embodiment, the locking mechanism 510 includes a fastener 512 pivotally coupled to the tibial base trial 436. The fastener 512 is permanently secured to the plate 442 of the tibial base trial 436, but it should be appreciated that in other embodiments the fastener may be removable from the tibial base trial or secured to the intramedullary orthopaedic surgical instruments.

The fastener 512 of the locking mechanism 510 includes a button head 514 positioned above the top surface 472 of the platform 470 and a central shaft 516 secured to the button head 514. The central shaft 516 extends through an opening (not shown) defined in the platform 470 to a lower end 518. An outer sleeve 520 is secured to the central shaft 516 between the lower end 518 and the lower surface 446 of the plate 442, thereby securing the fastener 512 to the base trial 436. As shown in FIG. 12, the fastener 512 includes a plurality of external threads 522 that are formed on the lower end 518 of the central shaft 516. The external threads 522 of the fastener 512 engage internal threads formed on an intramedullary surgical instrument 440 to secure the intramedullary surgical instrument 440 to the base trial 436.

For example, as shown FIG. 11, the intramedullary surgical instruments 440 include the broach 280, which is configured to be coupled to the base trial 436 via the fastener 512. As described above, the broach 280 has a bore 338 defined therein and an aperture 344 positioned below the bore 338. The aperture 344 is defined by a cylindrical wall 342 that has a plurality of internal threads 346 formed thereon. To secure the broach 280 to the base trial 436, the base trial 436 is aligned with the broach 280 and the lower end 518 of the fastener 512 is advanced into the bore 338. The external threads 522 formed on the fastener 512 are advanced into contact with the internal threads 346 of the broach 280. By rotating the fastener 512 about the longitudinal axis 530, the internal threads 346 are engaged with external threads 522, thereby securing the broach 280 to the base trial 436. When the base trial 436 is seated on the top surface 306 of the broach 280, the outer sleeve 520 of the fastener 512 is positioned in the bore 338 of the broach 280.

When the broach 280 is secured to the base trial 436, the base trial 436 is permitted to rotate relative to the broach 280. As described above, the pin 486 is received in the slot 356 when the broach 280 is secured to the base trial 436. The slot 356 is sized such that the pin 486 may move within the slot 356, thereby permitting the base trial 436 to rotate relative to the broach 280 during the orthopaedic surgical procedure.

The button head 514 of the fastener 512 includes a neck 524 that confronts the platform 470 of the base trial 436 and a knob 526 secured to the neck 524. The knob 526 has a knurled outer surface 528 that may be grasped by the surgeon to rotate the fastener 512 about the longitudinal axis 530. The button head 514 also has a socket 532 defined therein, which is sized to receive a driver or other surgical tool to rotate the fastener 512 about the axis 530.

Figure 14:
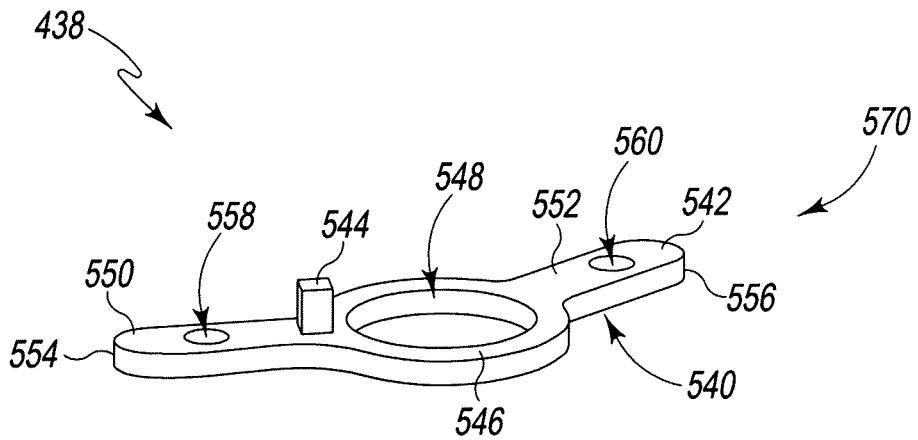
FIG. 14 is a perspective view of one embodiment of a base insert of the instrument group of FIG. 11.
Figure 15:
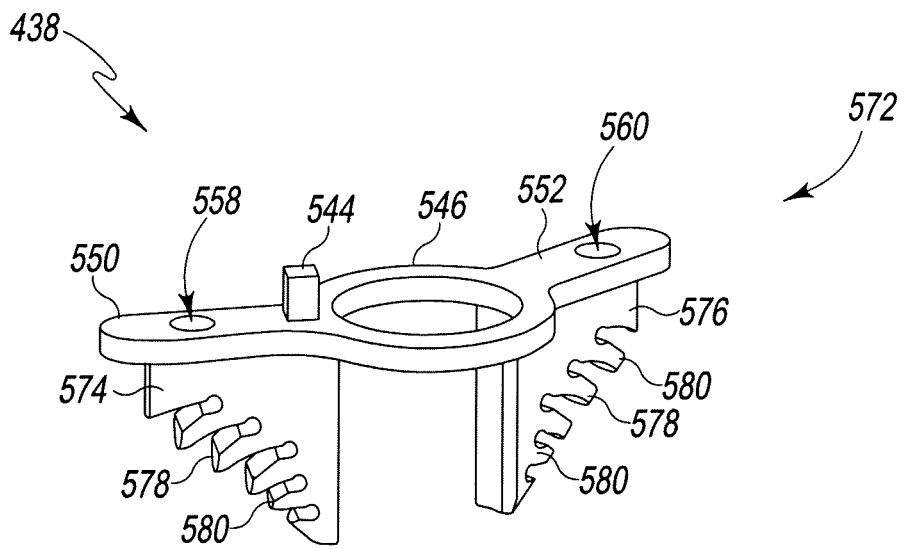
FIG. 15 is a perspective view of another embodiment of a base insert of the instrument group of FIG. 11.

Referring now to FIGS. 14 and 15, the system 10 further includes a pair of base inserts 438. The base inserts 438 are configured to be positioned separately in the plate opening 450 of the base trial 436. Each base insert 438 has a lower surface 540 configured to engage the shelf surface 468 of the base trial 436 when the base insert 438 is seated on the base trial 436 and an upper surface 542 positioned opposite the lower surface 540. The base insert 438 includes a central frame 546 sized to be received in the central opening 454 of the base trial 436. The central frame 546 has a cylindrical slot 548 defined therein, which is sized to receive the platform 470 of the base trial 436. A lug 544 extends upwardly from the upper surface 542 adjacent to the slot 548.

The base insert 438 also includes a pair of prongs 550, 552 that extend outwardly from the central frame 546 to ends 554, 556, respectively. The prongs 550, 552 are sized to be received in the elongated openings 456 of the base trial 436. The prong 550 has a bore 558 defined therein at the end 554 thereof. Similarly, the prong 552 has a bore 560 defined therein at the end 556 thereof. The bores 558, 560 are sized to receive pegs 562, 564 of the attachment tool 566, as described in greater detail below.

The base inserts 438 include a check insert 570 (see FIG. 14) and a keel punch insert 572 (see FIG. 15). The keel punch insert 572 includes a pair of lower arms 574, 476 that extend downwardly from the prongs 550, 552, respectively. Each of the lower arm 574, 576 includes a tapered outer surface 578 that has a plurality of cutting teeth 580 formed thereon.

Returning to FIG. 11, the system 10 includes the attachment tool 566, which may be used by the surgeon to attach and detach the base inserts 438 from the base trial 436. In the illustrative embodiment, the attachment tool 566 includes a main body 590 and a pair of arms 592, 594 extending outwardly from the main body 590. The main body 590 corresponds to the central frame 546 of the base insert 438, and the arms 592, 594 correspond to the prongs 550, 552, respectively, of the base insert 438. The attachment tool 566 has a lower surface 596 that engages the upper surface 542 of the base insert 438 when the base insert 438 is secured thereto.

Figure 16:
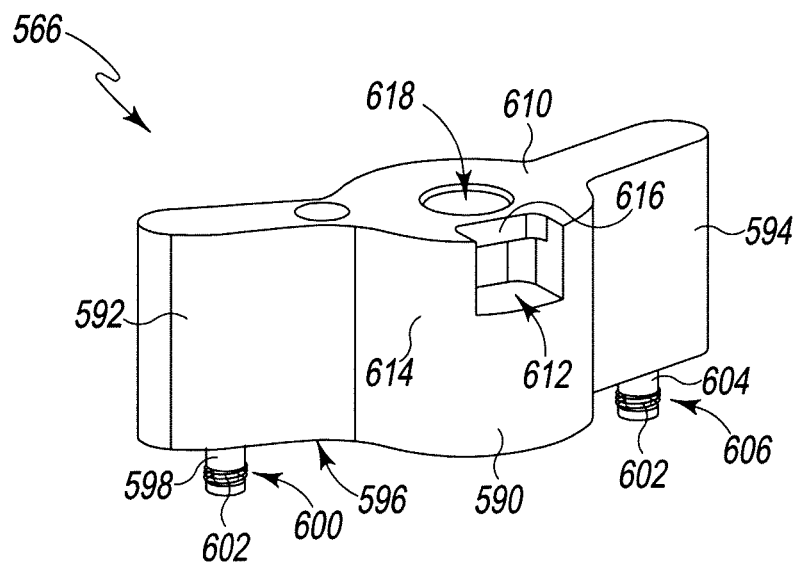
FIG. 16 is an elevation view of an insert attachment tool of the instrument group of FIG. 11.
Figure 17:
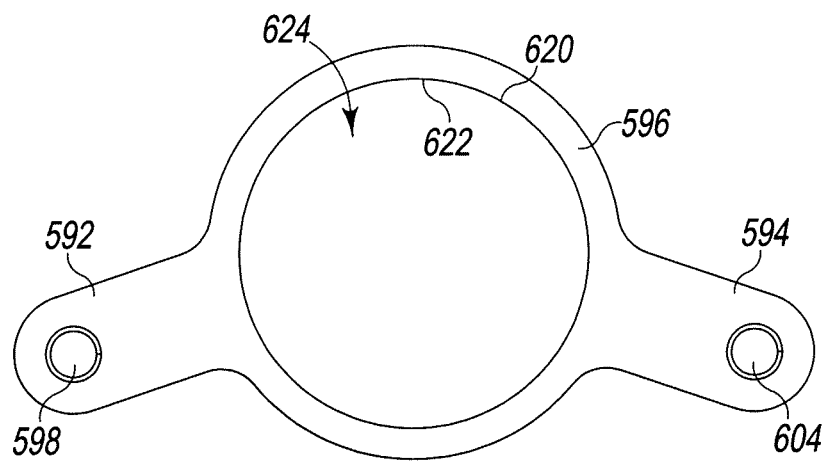
FIG. 17 is a plan view of the insert attachment tool of FIG. 16.

As shown in FIGS. 16 and 17, the arm 592 of the tool 566 has a peg 598 extending downwardly from the lower surface 596. The peg 598 is cylindrical and is sized to be received in the bore 558 defined in the end 554 of the prong 550. The peg 598 has an annular slot 600 defined therein, and a biasing element 602 is positioned in the slot 600. The biasing element 602 is configured to engage the prong 550 when the peg 598 is positioned in the bore 558 to secure the base insert 438 to the attachment tool 566. In the illustrative embodiment, the biasing element 602 is a ring-shaped coil. It should be appreciated that in other embodiments the spring may take the form of another biasing or friction element, such as, for example, an o-ring or a retaining ring.

The other arm 594 of the tool 566 also has a peg 604 extending downwardly from the lower surface 596. The peg 604 is cylindrical and is sized to be received in the bore 560 defined in the end 556 of the prong 552. The peg 604 has an annular slot 606 defined therein, and a biasing element 602 is positioned in the slot 600. The biasing element 602 is configured to engage the prong 552 when the peg 604 is positioned in the bore 560 to secure the base insert 438 to the attachment tool 566.

The attachment tool 566 has an upper surface 610 positioned opposite the lower surface 596. The main body 590 has a slot 612 that extends through the upper surface 610 and inwardly from the outer surface 614. As shown in FIG. 16, the main body 590 also includes a flange 616 that extends into the slot 612. The main body 590 also includes a central bore 618 that is defined in the upper surface 610.

As shown in FIG. 17, the lower surface 596 of the attachment tool 566 has an opening 620 defined therein. An inner wall 622 extends inwardly from the opening 620 to define an aperture 624 in the main body 590 of the tool 566. The aperture 624 is sized to receive the button head 514 of the fastener 512 when the tool 566 is secured to the base insert 438 on the base trial 436.

Figure 18:
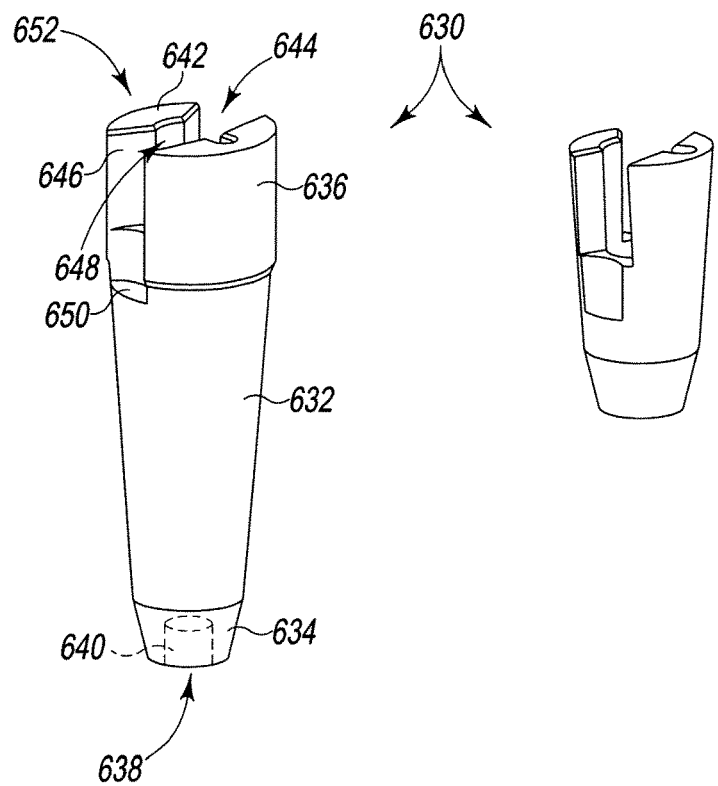
FIG. 18 is a perspective view of a number of modular stems of the instrument group of FIG. 11.

Returning to FIG. 11, the system 10 includes a number of intramedullary orthopaedic surgical instruments 440 that are configured to be coupled to the base trial 436. The instruments 440 include the broach 280, the stem trial 20, and a modular stem 630. It should be appreciated that other modular stems having different configurations may be provided. For example, as shown in FIG. 18, the outer diameter and/or length of the modular stem may vary to produce different sized canals to accommodate prosthetic components of different sizes.

The modular stem 630 includes an outer surface 632 extending from a tip 634 to an upper end 636. The outer surface 632 is tapered, with the diameter of the modular stem 630 decreasing from the upper end 636 to the tip 634. As shown in FIG. 18, the tip 634 of the modular stem 630 has an aperture 638 defined therein. An inner wall 640 defines the aperture 638, and the inner wall 640 has a plurality of internal threads (not shown) formed thereon. As described above, the stem trial 20 includes a plurality of external threads 274, and the aperture 638 is sized to receive the upper end 272 of the stem trial 20 such that the internal threads engage with the external threads 274 to thereby secure the stem trial 20 to the modular stem 630.

Figure 19:
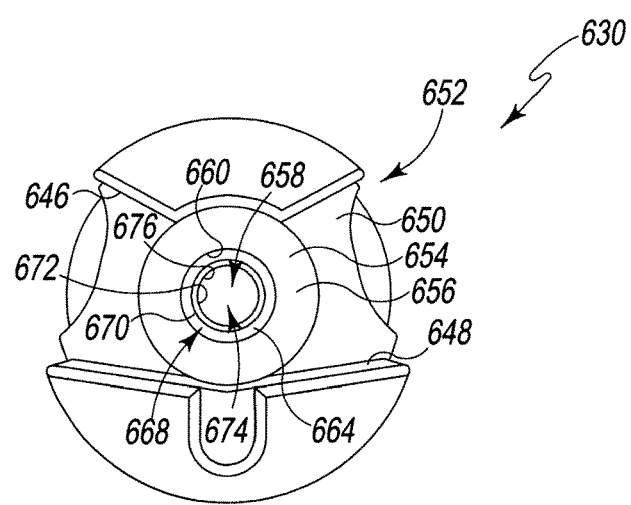
FIG. 19 is a plan view of one of the modular stems of FIG. 18.

The modular stem 630 includes a substantially planar top surface 642 at the upper end 636 thereof. An opening 644 is defined in the top surface 642, and the modular stem 630 has inner walls 646, 648 that extend downwardly from the top surface 642. The inner walls 646, 648 cooperate with a bottom wall 650 to define a slot 652 in the modular stem 630. As shown in FIGS. 18 and 19, the slot 652 extends through the outer surface 632 of the modular stem 630.

A platform 654 extending upwardly from the bottom wall 650 is positioned in the slot 652. The platform 654 has a top surface 656 and an opening 658 defined in the top surface 656. A cylindrical wall 660 extends inwardly from the opening 658 to a lower surface 664. The lower surface 664 and the cylindrical wall 660 cooperate to define a bore 668 in the platform 654. As shown in FIG. 19, the lower surface 664 has another opening 670 defined therein, and another cylindrical wall 672 extends inwardly from the opening 670. The cylindrical wall 672 defines an aperture 674 within the modular stem 630 and has a plurality of internal threads 676 formed thereon.

To secure the modular stem 630 to the base trial 436, the base trial 436 is aligned with the modular stem 630 and the lower end 518 of the fastener 512 is advanced into the bore 668. The external threads 522 formed on the fastener 512 are advanced into contact with the internal threads 676 of the modular stem 630. By rotating the fastener 512 about the longitudinal axis 530, the internal threads 676 are engaged with external threads 522, thereby securing the modular stem 630 to the base trial 436. When the base trial 436 is seated on the top surface 656 of the modular stem 630, the outer sleeve 520 of the fastener 512 is positioned in the bore 668 of the modular stem 630.

As described above, the system 10 also includes a number of tibial bearing trial assemblies 434. An tibial bearing trial assembly 434 is disclosed in U.S. Patent App. Ser. No. 61/503,300, filed Jun. 30, 2011 and entitled "TRIALING SYSTEM FOR A KNEE PROSTHESIS AND METHOD OF USE," by Thomas E. Wogoman et al., which is incorporated herein by reference. It should be appreciated that in other embodiments the tibial bearing trial may be a monolithic component, and the system 10 may include multiple tibial bearing trials different sizes and configurations.

Figure 20:
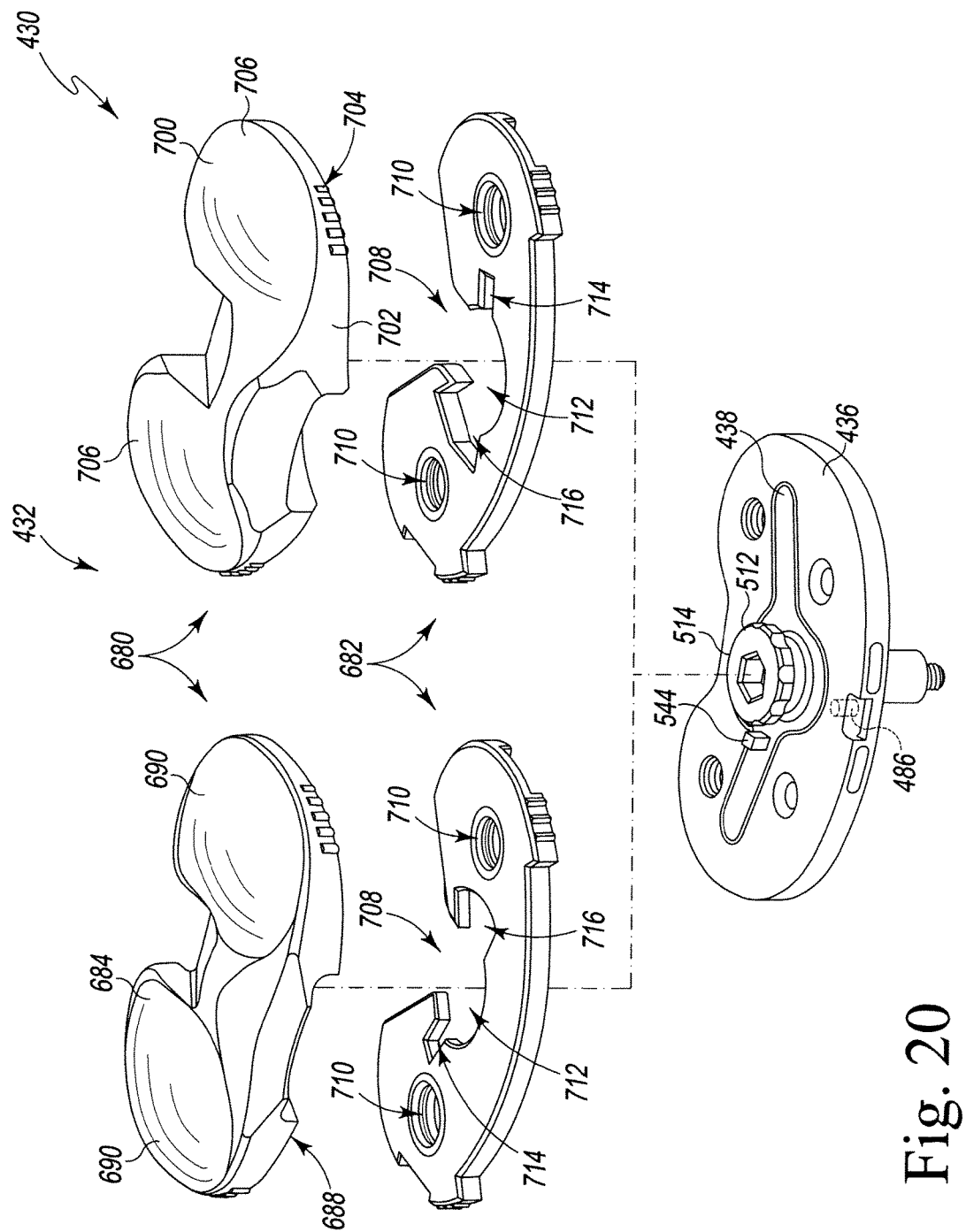
FIG. 20 is an exploded perspective view of a tibial base trial, a base insert, and a number of tibial bearing trials.

Referring now to FIG. 20, each tibial bearing trial assembly 434 is a multi-piece assembly configured to assist the surgeon in selecting a size and configuration of a prosthetic tibial bearing component of the knee prosthesis. A tibial bearing trial 434 may be assembled with one of a number of tibial bearing surface trials 680 and one of a number of a plurality of trial shims 682. Each bearing surface trial 680 has a different size and/or configuration, and each shim 682 has a different thickness. Because each shim 682 is configured to be secured to each bearing surface trial 680, the surgeon is able to assemble a tibial bearing trial 434 of one size and configuration, evaluate the performance of that tibial bearing trial 434, and then modify the tibial bearing trial 434 as necessary to determine intraoperatively the type and configuration of the prosthetic tibial bearing component to be implanted.

As shown in FIG. 20, one of the bearing surface trials 680 is a fixed bearing surface trial 684. The term "fixed bearing surface trial" as used herein refers to a bearing surface trial that is fixed in position relative to the tibial base trial 436 when the bearing surface trial and shim are attached thereto (i.e., it is configured to not substantially rotate or move in the anterior-posterior direction or medial-lateral direction relative to the tibial base trial 436). The fixed bearing surface trial 684 may be embodied as a cruciate retaining trial, a posterior stabilized trial, a revision trial, or other surface trial configuration, per the surgeon's preference. For example, in embodiments where the fixed bearing surface trial 684 is embodied as a posterior stabilized trial, the fixed bearing surface trial 684 may include a spine extending upwardly from the upper bearing surface of the trial 684.

The fixed bearing surface trial 684 has a platform 686 including a lower surface 688 that contacts the shim 682 when the shim 682 is secured thereto. The platform 686 also includes a pair of articulation surfaces 690 that are positioned opposite the lower surface 688. The articulation surfaces 690 are configured to rotate with the condyle surfaces of a femoral surgical instrument of a femoral prosthetic component.

The other bearing surface trial 680 is embodied as a mobile bearing surface trial 700. The term "mobile bearing surface trial" as used herein refers to a bearing surface trial that is permitted to rotate relative to the tibial base trial 436 when the bearing surface trial and the shim are attached thereto (i.e., it is configured to substantially rotate or move in the anterior-posterior direction or the medial-lateral direction relative to the tibial base trial 436). The mobile bearing surface trial 700 may be embodied as a cruciate retaining trial, a posterior stabilized trial, a revision trial, or other surface trial configuration, per the surgeon's preference. For example, in embodiments where the mobile bearing surface trial 700 is embodied as a posterior stabilized trial, the mobile bearing surface trial 700 may include a spine extending upwardly from the upper bearing surface thereof.

The mobile bearing surface trial 700 has a platform 702 including a lower surface 704 the shim 682 when the shim 682 is secured thereto. The platform 702 also includes a pair of articulation surfaces 706 that are positioned opposite the lower surface 704. The articulation surfaces 706 are configured to rotate with the condyle surfaces of a femoral surgical instrument or femoral prosthetic component.

As described above, the surface trials 684, 700 are configured to be secured with a trial shim 682. The shim 682 has an aperture 708 defined therein, which is configured to receive the button head 514 of the fastener 512 secured to the base trial 436 and the lug 544 of the base insert 438 when the shim 682 is positioned on the base trial 436. Each shim 682 also includes a pair of through-holes 710, which are configured to receive fastener pegs (not shown) of the tibial bearing surface trials 680 to secure the shim 682 to each trial 680.

The aperture 708 also includes a central passageway 712, a rectangular slot 714 extending outwardly from the central passageway 712, and an arcuate slot 716. The central passageway 712 is sized to receive the button head 514. As will be described in greater detail below, the rectangular slot 714 is sized to receive the lug 544 when the shim 682 is attached to a fixed bearing surface trial 684 on the base trial 436. The arcuate slot 716 is also sized to receive the lug 544 when the shim 682 is attached to a mobile bearing surface trial 700, thereby permitting the mobile bearing surface trial 700 to rotate relative to the base trial 436.

Figure 21A:
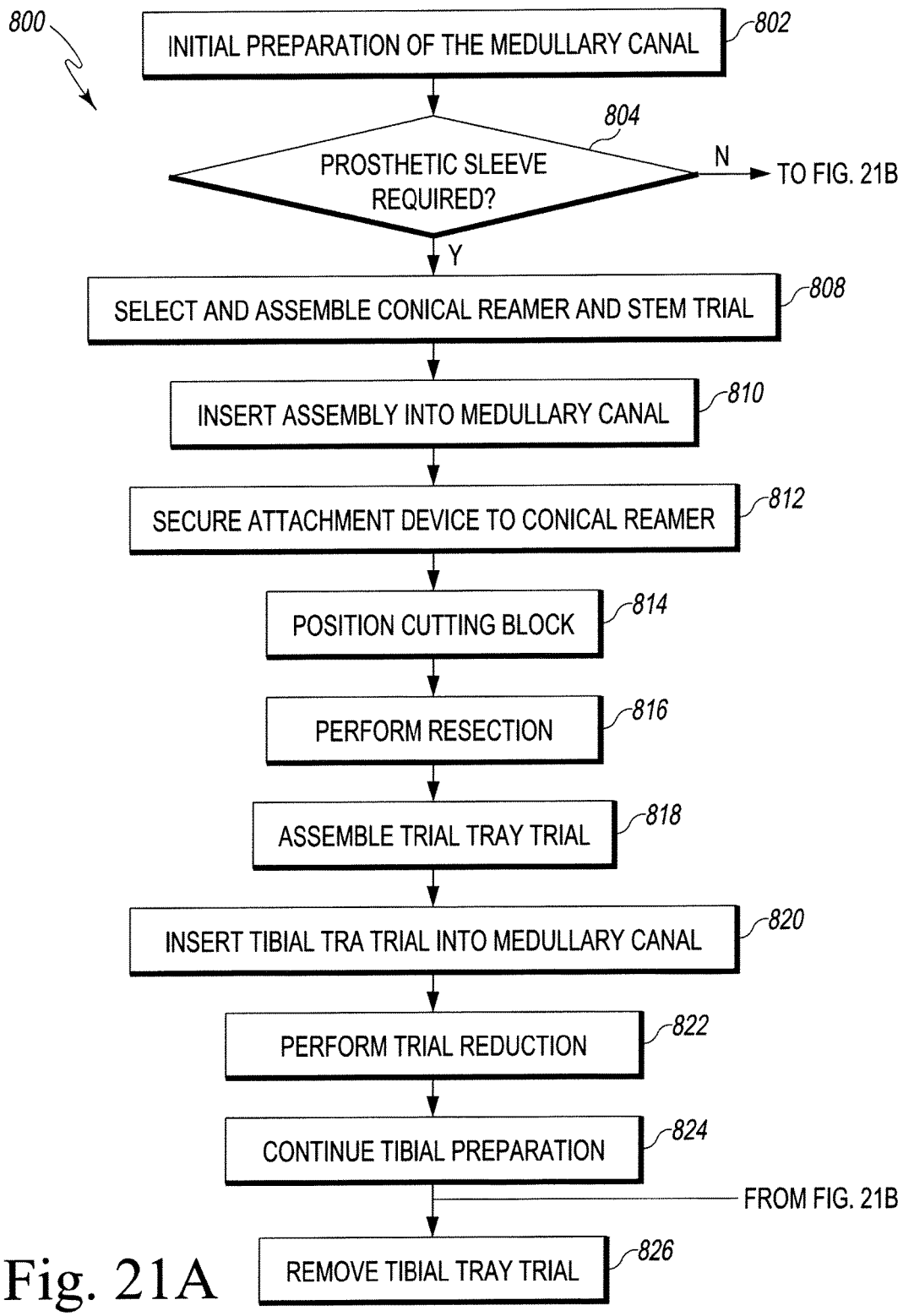
FIGS. 21A and 21B are a simplified flow chart of one embodiment of a procedure utilizing the orthopaedic surgical instrument system of FIGS. 1-20.
Figure 21B:
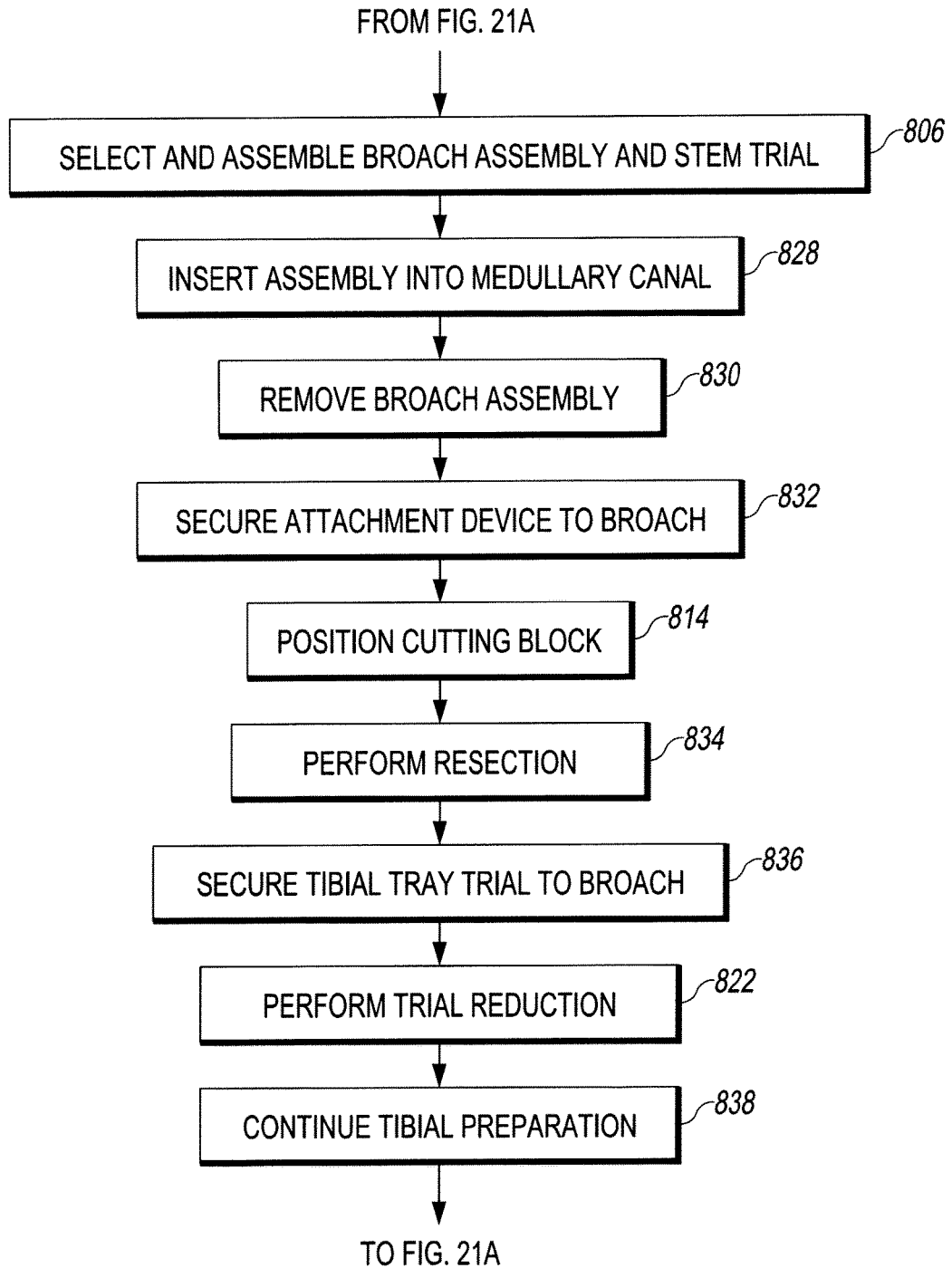

The system 10 may be utilized during the performance of an orthopaedic surgical procedure similar to that shown in FIGS. 21A and 21B. As shown in FIGS. 22-24 and 30-32, the surgeon may initially prepare the medullary canal and determine whether the patient requires a tibial sleeve. The surgeon may then insert an intramedullary orthopaedic surgical instrument 16, such as, for example, the surgical reamer 18 or the broach assembly 22 into the medullary canal. The surgeon may secure the attachment device 12 and the cutting block 14 to the intramedullary orthopaedic surgical instrument 16 and perform a resection of the patient's tibia.

As shown in FIGS. 25-29, the surgeon may assemble a tibial tray trial 432 and perform a trial reduction with a tibial bearing trial 434. The surgeon may then impact a keel punch insert 572 into the patient's tibia before removing the tibial tray trial 432 therefrom.

Figure 22:
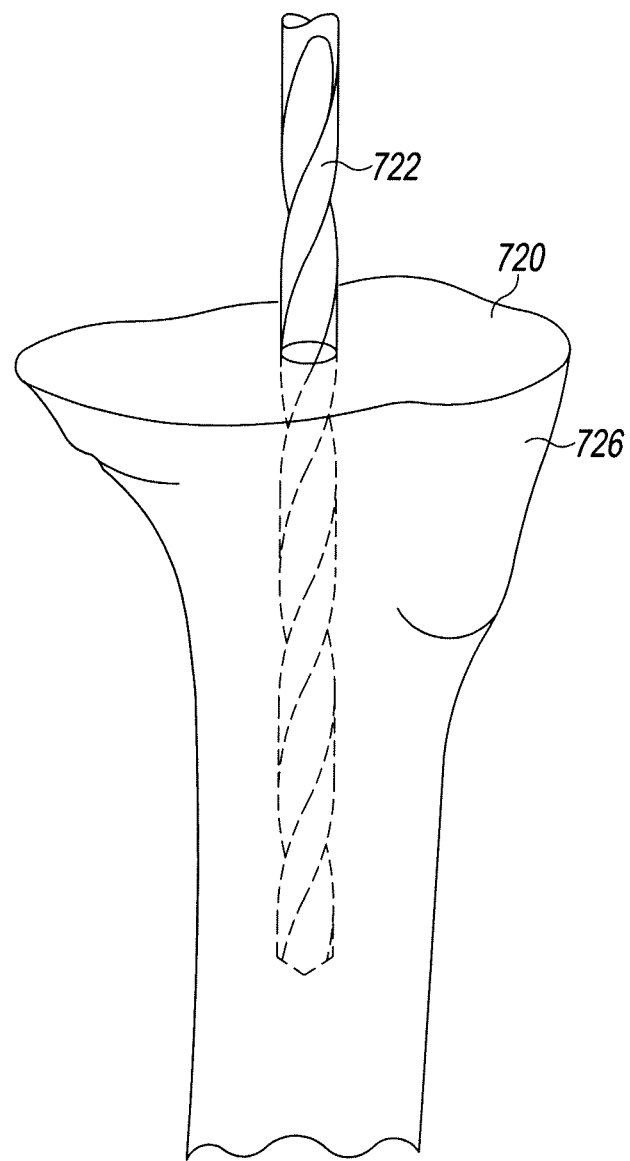
FIGS. 22-33 are views of a patient's tibia and the orthopaedic surgical instrument system of FIGS. 1-20 as the orthopaedic surgical instrument system is used in the procedure of FIG. 21.

Referring now to FIGS. 21A and 21B, an illustrative orthopaedic surgical procedure 800 utilizing the system 10 is shown. In procedure block 802, a medullary canal 254 of a patient's tibia 720 is initially prepared. To do so, an orthopaedic surgeon may insert an initial surgical reamer 722 into the medullary canal 254. As shown in FIG. 22, the surgeon may use the reamer 722 to drill and/or ream the medullary canal 254 to the depth and/or diameter required receive the intramedullary orthopaedic surgical instrument 16. Multiple drills or reamers may be used to increase the size of the opening 724 of the medullary canal 254 formed on the proximal end 726 of the patient's tibia 720.

In procedure block 804 of the surgical procedure 800, the surgeon determines whether a prosthetic sleeve will be included with the tibial prosthetic component. The surgeon may make this determination pre-operatively or intraoperatively, depending on the condition of the patient's tibia 720. If the surgeon determines a prosthetic sleeve is necessary, the procedure 800 advances to procedure block 806 in FIG. 21B. If a prosthetic sleeve is unnecessary, the procedure 800 advances to procedure block 808.

In procedure block 808, the surgeon selects a surgical reamer 18 and a stem trial 20. As described above, multiple surgical reamers 18 and/or stem trials 20 may be provided to accommodate prosthetic components of different sizes. When the surgeon has selected a reamer 18 and the stem trial 20, the surgeon may assemble the instruments to form an intramedullary orthopaedic surgical instrument 16. To do so, the surgeon aligns the upper end 272 of the stem trial 20 with the aperture 248 defined in the tip 244 of the reamer 18. The surgeon may advance the upper end 272 of the trial 20 into contact with the inner wall 250 of the reamer 18 to engage the external threads 274 formed on the trial 20 with the internal threads of the reamer 18. The surgeon may thread the trial 20 into the reamer 18 to secure the instruments together.

Figure 23:
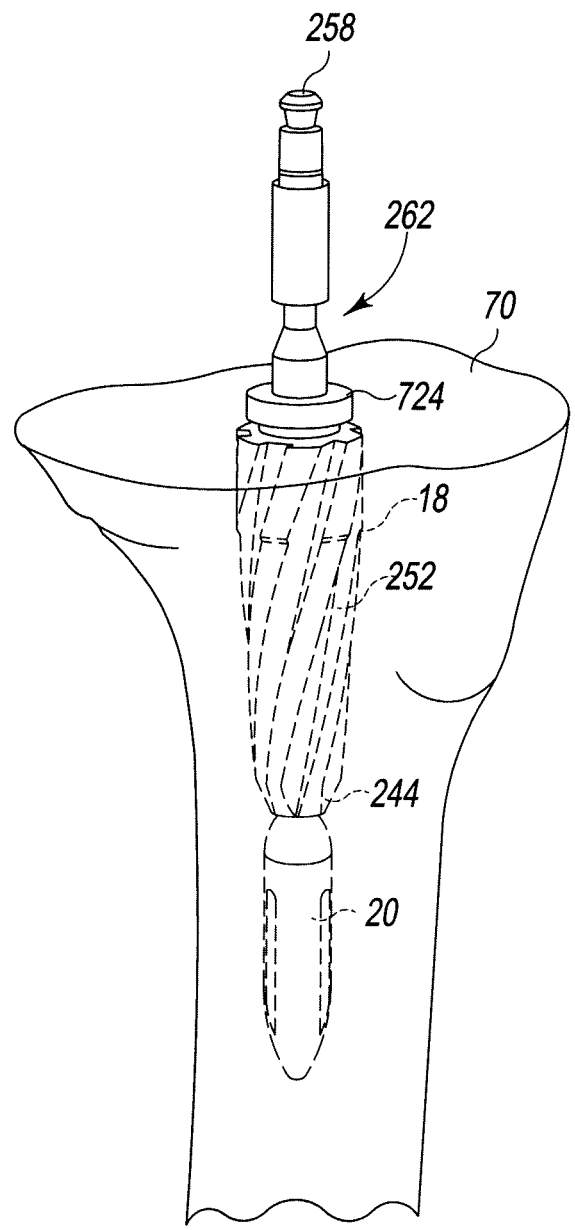

After the intramedullary orthopaedic surgical instrument 16 is assembled, the procedure 800 advances to procedure block 810. In block 810, the surgeon advances the intramedullary orthopaedic surgical instrument 16 into the medullary canal 254, as shown in FIG. 23. To do so, the surgeon may secure the shank 242 of the reamer 18 to a power tool and engage the cutting flutes 252 of the reamer 18 with the patient's tibia 720. The surgeon may then operate the power tool to drill or ream the patient's tibia 720 with the reamer 18 and insert the reamer 18 and the stem trial 20 to the required depth.

When the intramedullary orthopaedic surgical instrument 16 is properly positioned in proximal end 726 of the patient's tibia 720, the surgeon may secure the attachment device 12 to the shank 242 of the reamer 18 in procedure block 812. To do so, the surgeon aligns the passageway 64 of the attachment base 30 with the upper end 258 of the shank 242. The surgeon may then press on the handles 82 of the levers 72 in the direction indicated by arrows 730 in FIG. 24 to rotate the levers 72 and remove the catches 78 from the passageway 64. The surgeon may advance the attachment base 30 downward over the shank 242 until the lower end 42 of the base 30 engages the platform 256 of the reamer 18. The surgeon may release the handles 82, thereby permitting the springs 100 to rotate the levers 72 into the engaged position. In that position, the catches 78 are received in the recess 262 formed in the shank 242, thereby securing the attachment device 12 to the reamer 18.

Figure 24:
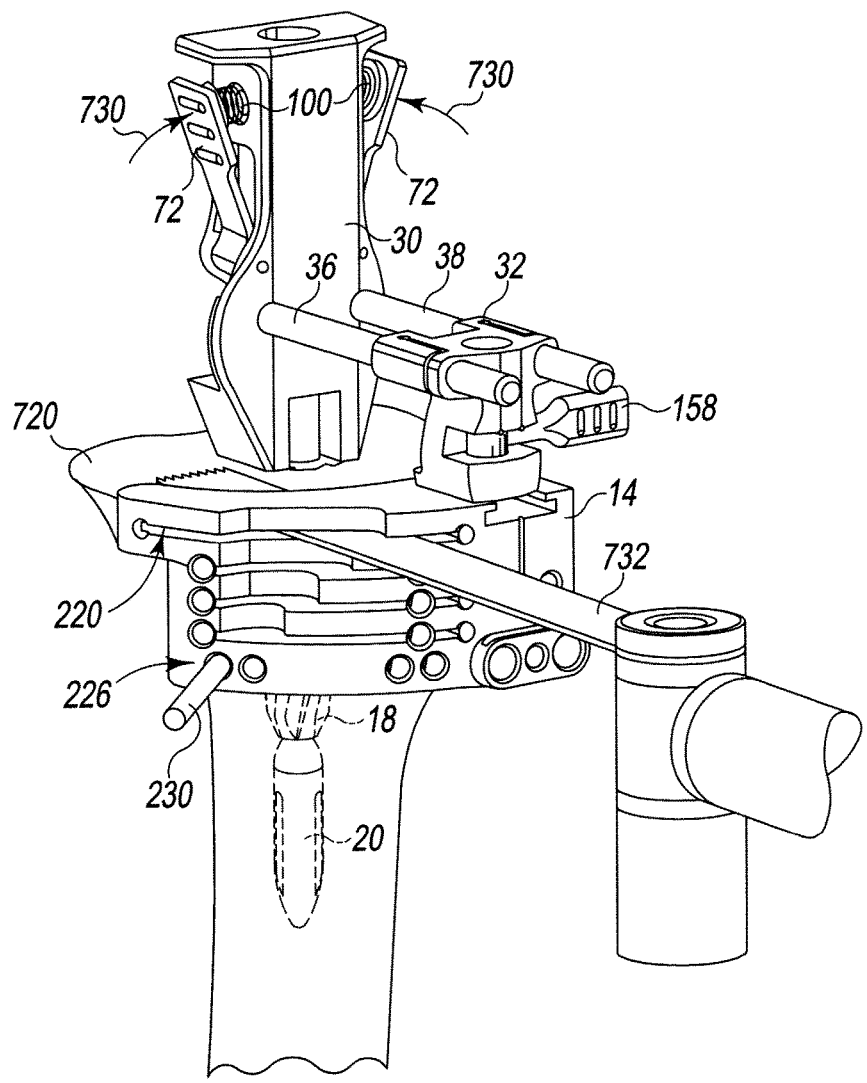

Returning to FIG. 21A, the procedure 800 advances to procedure block 814 in which the cutting block 14 is moved into position for the resection of the proximal end 726 of the patient's tibia 720. To do so, the surgeon may secure the cutting block 14 to the mounting frame 32, as shown in FIG. 24. In the illustrative embodiment, the surgeon may grasp the control knob 158 and operate the control knob 158 to move the plug 150 to the disengaged position. The surgeon may then align the slot 210 of the cutting block 14 with the plug 150 and the apertures 172 with the alignment pins 170 of the mounting frame 32. The cutting block 14 may be advanced over the plug 150 and the alignment pins 170, and the surgeon may operate the control knob 158 to rotate the plug 150 such that the flanges 152 of the plug 150 are received in the channel 154 defined in the cutting block 14, thereby securing the cutting block 14 to the mounting frame 32. The surgeon may position the mounting frame 32 on the rails 36, 38 of the attachment base 30 and slide the mounting frame 32 (and hence cutting block 14) into position relative to the tibia 720.

After the cutting block 14 is positioned, the surgeon may perform the resection in procedure block 816. To do so, the surgeon may use the cutting guides 220 defined in the cutting block 14, as shown in FIG. 24. For example, the surgeon may select the cutting guide 220 of the cutting block 14 corresponding to a desired amount of bone to be removed. The surgeon may perform the resection by inserting a bone saw blade 732 into the selected cutting guide 220 of the cutting block 14. The resection removes a proximal portion of the patient's tibia 720 to create a substantially planar proximal surface 734.

The surgeon may also utilize fastener guides 226 to attach one or more fixation pins 230 to the patient's tibia 720. After securing the cutting block 14 to the tibia 720 with fixation pins 230, the surgeon may remove the attachment device 12, the reamer 18, and the stem trial 20 from the tibia 720 prior to performing the resection.

Figure 25:
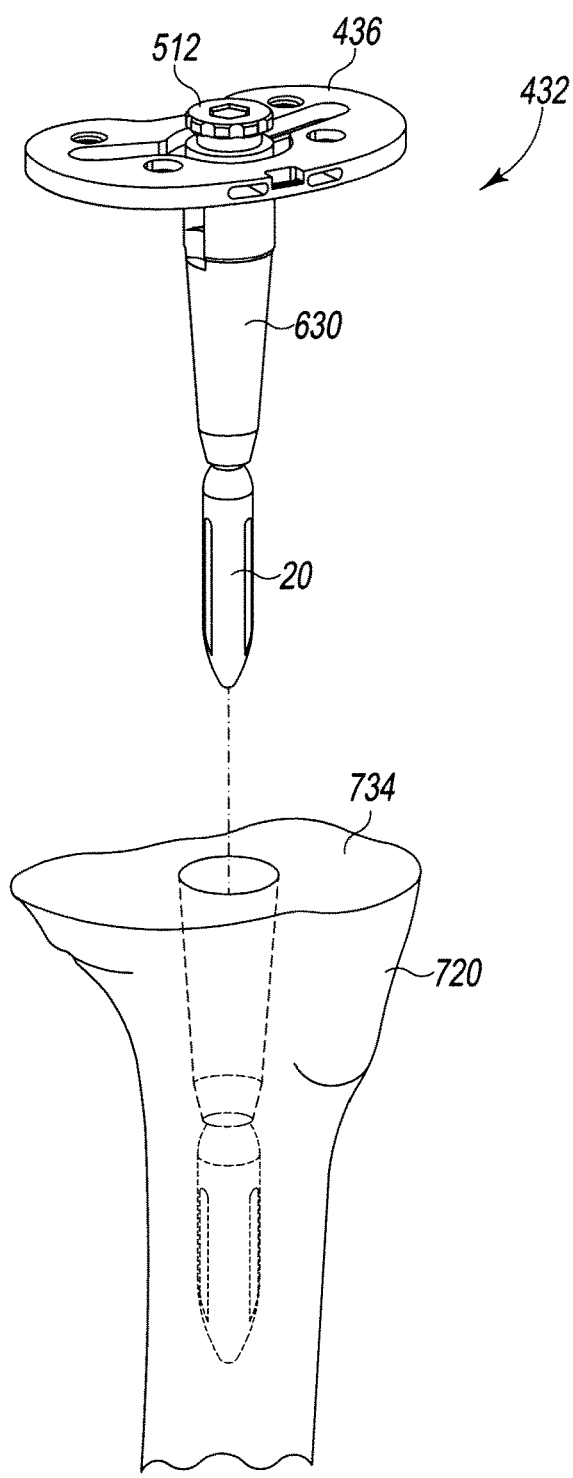

After performing the resection, the surgeon may assemble a tibial tray trial 432 in procedure block 818. To do so, the surgeon may select a base trial 436 and a modular stem 630 and secure those instruments together with the stem trial 20, as shown in FIG. 25. To secure the modular stem 630 to the base trial 436, the base trial 436 is aligned with the modular stem 630 and the lower end 518 of the fastener 512 is advanced into the bore 668. The external threads 522 formed on the fastener 512 are advanced into contact with the internal threads 676 of the modular stem 630. By rotating the fastener 512 about the longitudinal axis 530, the internal threads 676 are engaged with external threads 522, thereby securing the modular stem 630 to the base trial 436. When the base trial 436 is seated on the top surface 656 of the modular stem 630, the outer sleeve 520 of the fastener 512 is positioned in the bore 668 of the modular stem 630.

To secure the stem trial 20 to the modular stem 630, the surgeon may align the upper end 272 of the stem trial 20 with the aperture 638 defined in the tip 634 of the modular stem 630. The surgeon may advance the upper end 272 of the trial 20 into contact with the inner wall 640 of the modular stem 630 to engage the external threads 274 formed on the trial 20 with the internal threads of the modular stem 630. The surgeon may thread the trial 20 into the modular stem 630 to secure the instruments together.

In the procedure block 820, the tibial tray trial 432 is inserted into the medullary canal 254 of the patient's tibia 720. To do so, the surgeon may align the stem trial 20 and the modular stem 630 with the opening 724 of the canal 254, as shown in FIG. 25. The surgeon may then advance the tibial tray trial 432 downward such that the stem trial 20 and the modular stem 630 are positioned in the medullary canal 254 and the tibial base trial 436 is engaged with the surgically-prepared proximal surface 734 of the tibia 720.

Figure 26:
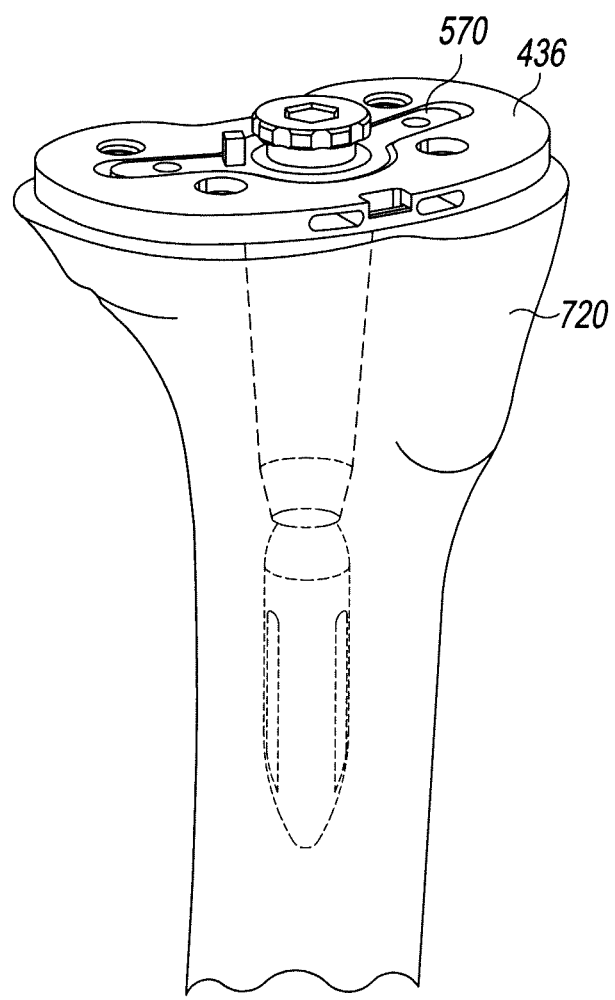

After the tibial tray trial 432 is positioned, the surgeon may perform a trial reduction in procedure block 822. To do so, the surgeon may position the check insert 570 in the plate opening 450 defined in the tibial base trial 436 as shown in FIG. 26. Once the selected check insert 570 is properly seated, the surgeon may select a trial shim 682 and a tibial bearing surface trial 680.

Figure 27:
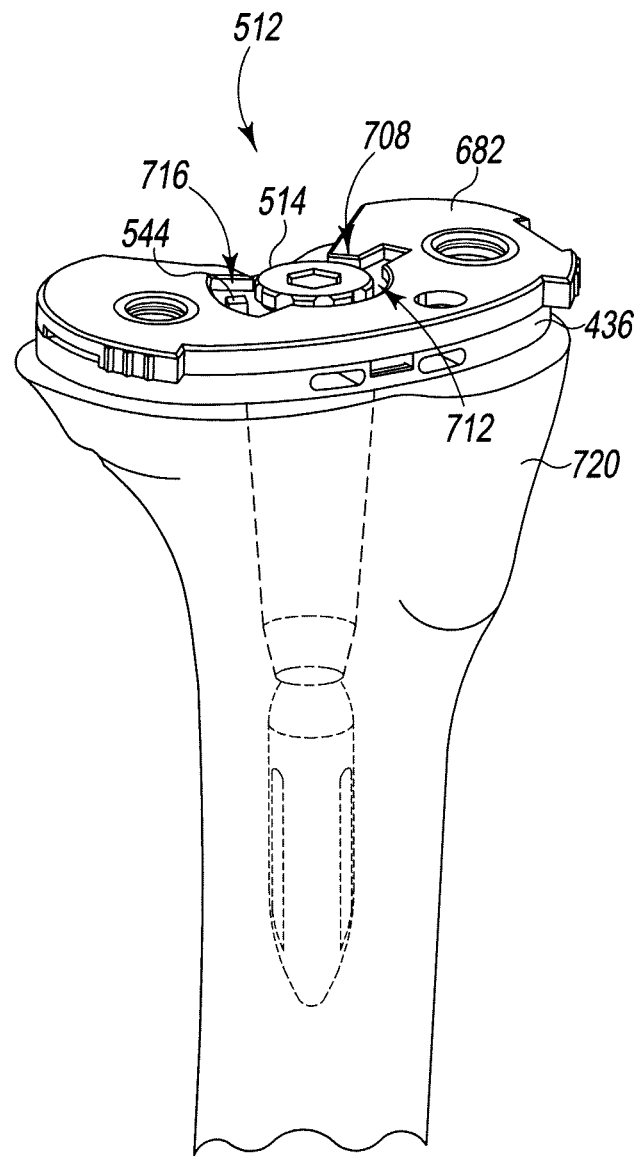

For example, if the surgeon desires a mobile bearing trial, the surgeon may position the selected trial shim 682 on the tibial tray trial 432. As shown in FIG. 27, the surgeon aligns the aperture 708 of the shim 682 with the button head 514 of the fastener 512 and the lug 544 of the insert 570. The surgeon then places the shim 682 over the button head 514 and the lug 544 to seat the shim 682 on the base trial 436. When properly seated, the lug 544 is received in the slot 716 of the shim 682.

The surgeon may select a mobile bearing surface trial 700 and attach the trial 700 to the shim 682. To do so, the surgeon aligns the through-holes 710 of the shim 682 with the pegs of the bearing surface trial 700. The surgeon then advances the pegs into the respective through-holes 710 such that the lower surface 704 of the mobile bearing surface trial 700 is placed in contact with the shim 682 to assemble the mobile bearing trial.

The surgeon may extend the knee and note the anteroposterior stability, medial-lateral stability, and overall alignment in the A/P and M/L planes. The surgeon may also able to assess the bearing rotation and patellofemoral tracking because the mobile bearing surface trial 700 is rotatable relative to the base trial 436. The surgeon may continue to try various combinations of shims 682 and bearing surface trials 700 to ascertain which implant size and configuration (e.g., the thickness of the implant, the mobility of the implant, etc.) will have the best stability in flexion and extension while permitting the desired kinematics.

If the surgeon desires a fixed bearing trial, the surgeon may select a fixed bearing surface trial 684 and secure the trial 684 to the shim 682. The surgeon may then position the selected trial shim 682 (and bearing surface trial 684) on the tibial tray trial 432. The surgeon may align the aperture 708 of the shim 682 with the button head 514 of the fastener 512 and the lug 544 of the insert 570. The surgeon may then place the shim 682 over the button head 514 and the lug 544 to seat the shim 682 on the base trial 436. When properly seated in the fixed bearing orientation, the lug 544 is received in the slot 714 of the shim 682 such that the shim 682 (and hence bearing surface trial 684) is not permitted to rotate relative to the base trial 436.

When the fixed bearing surface trial 684 is in place, the surgeon carefully extends the knee of the patient, noting the anteroposterior stability, medial-lateral stability, and overall alignment in the anterior-posterior ("A/P") plane and medial-lateral ("M/L") plane. Rotational alignment of the tibial base trial 436 may be adjusted with the knee moving through the range of motion, rotating the trial 436, shim 682, and the bearing trial 684. The surgeon sets the rotation of the base trial 436 by assessing multiple factors including femoral position and tibial plateau coverage. The surgeon may continue to try various combinations of shims 682 and bearing surface trials 684 to ascertain which implant size and configuration (e.g., the thickness of the implant, the mobility of the implant, etc.) will have the best stability in flexion and extension while permitting the desired kinematics. After completing trial reduction, the surgeon may fix the tibial tray trial 432 into position by inserting one or more fixation pins into the fastener guides 498.

Figure 28:
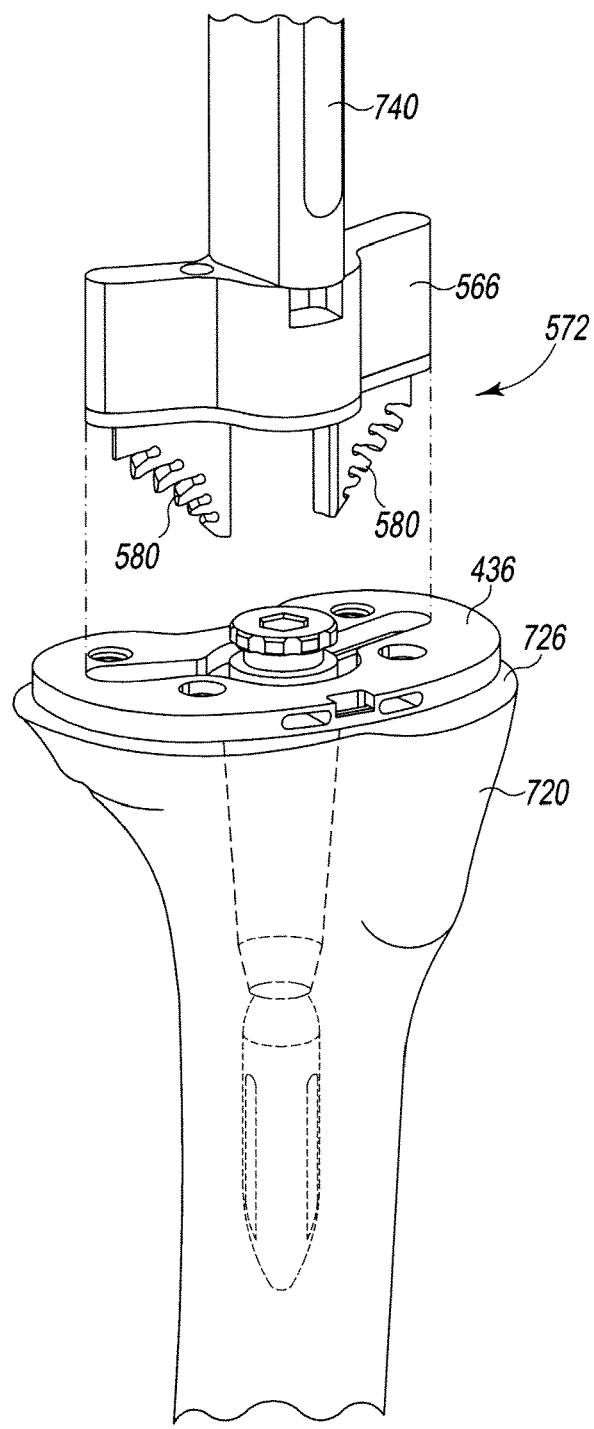

Returning to FIG. 21A, the procedure 800 may advance to procedure block 824 in which the surgeon continues the tibial preparation by impacting the keel punch insert 572 into the proximal end 726 of the tibia 720. To do so, the surgeon removes the check insert 570 from the base trial 436, as shown in FIG. 28. The surgeon may then secure the punch insert 572 to the attachment tool 566 by aligning the pegs 598, 604 of the attachment tool 566 with the bores 558, 560, respectively, of the punch insert 572 and advancing the pegs 598, 604 into the bores 558, 560.

The surgeon may secure the attachment tool 566 to an impaction handle 740 by engaging a catch (not shown) of the impaction handle 740 with the flange 616 formed on the attachment tool 566. After securing the handle 740 to the tool 566 and the punch insert 572, the surgeon may align the lower arms 574, 576 of the punch insert 572 with the passageways 460, 462 defined in the base trial 436. The surgeon may then advance the punch insert 572 downward such that the lower arms 574, 576 pass through the passageways 460, 462 and into the proximal end 726 of the tibia 720.

The surgeon may then drive the punch insert 572 into the tibia 720 by striking the handle 740 with mallet, sledge, or other impaction tool. As the punch insert 572 is driven into the bone, the cutting teeth 580 of the punch insert 572 engage the patient's tibia 720 to form additional slots (not shown) in the tibia 720. When the punch insert 572 is seated on the tibial base trial 436, the lower arms 574, 576 extend outwardly from the slot 652 defined in the modular stem 630.

Figure 29:
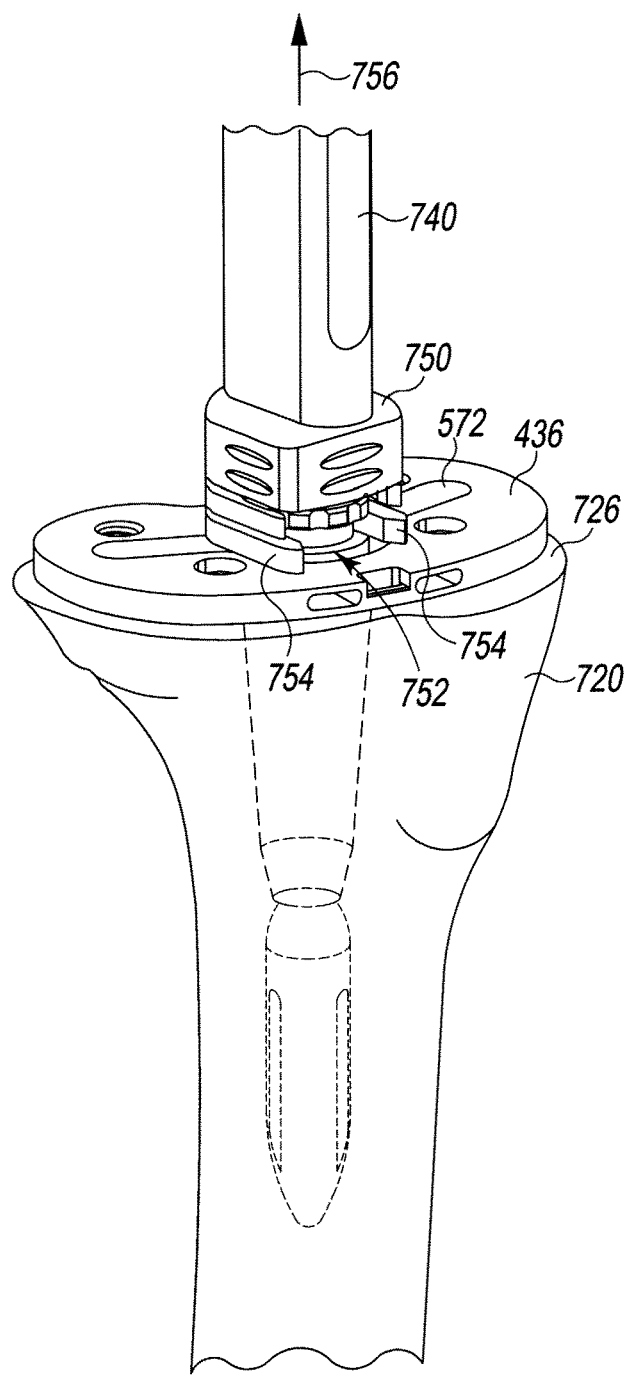

After the keel punch insert 572 has been driven into the tibia 720, the procedure 800 may advance to the procedure block 824. In block 824, the surgeon may remove the tibial tray trial 432 and the punch insert 572 from the proximal end 726 of the patient's tibia 720. To do so, the surgeon may attach a removal tool 750 to the impaction handle 740, as shown in FIG. 29. The removal tool 750 has a slot 752 defined therein sized to receive the button head 514 of the fastener 512 and a pair of engagement arms 754 configured to be positioned between the button head 514 and the plate 442 of the tibial base trial 436. When the removal tool 750 is positioned as shown in FIG. 29, the surgeon may pull in the direction indicated by arrow 756 to disengage the tibial tray trial 432 and the punch insert 572 from the tibia 720 such that the surgeon may proceed with the implantation of the prosthetic components.

Returning to block 804, if the surgeon determines a prosthetic sleeve is necessary, the procedure 800 advances to procedure block 806 in FIG. 21B. In procedure block 806, the surgeon selects a stem trial 20 and a broach assembly 22. As described above, multiple stem trials 20 and/or broach assemblies 22 may be provided to accommodate prosthetic components of different sizes. When the surgeon has selected a stem trial 20 and the broach assembly 22, the surgeon may assemble the instruments to form an intramedullary orthopaedic surgical instrument 16. To do so, the surgeon aligns the upper end 272 of the stem trial 20 with the aperture 302 defined in the tip 286 of the broach 280. The surgeon may advance the upper end 272 of the trial 20 into contact with the inner wall 304 of the broach 280 to engage the external threads 274 formed on the trial 20 with the internal threads of the reamer 18. The surgeon may thread the trial 20 into the broach 280 to secure the instruments together.

Figure 30:
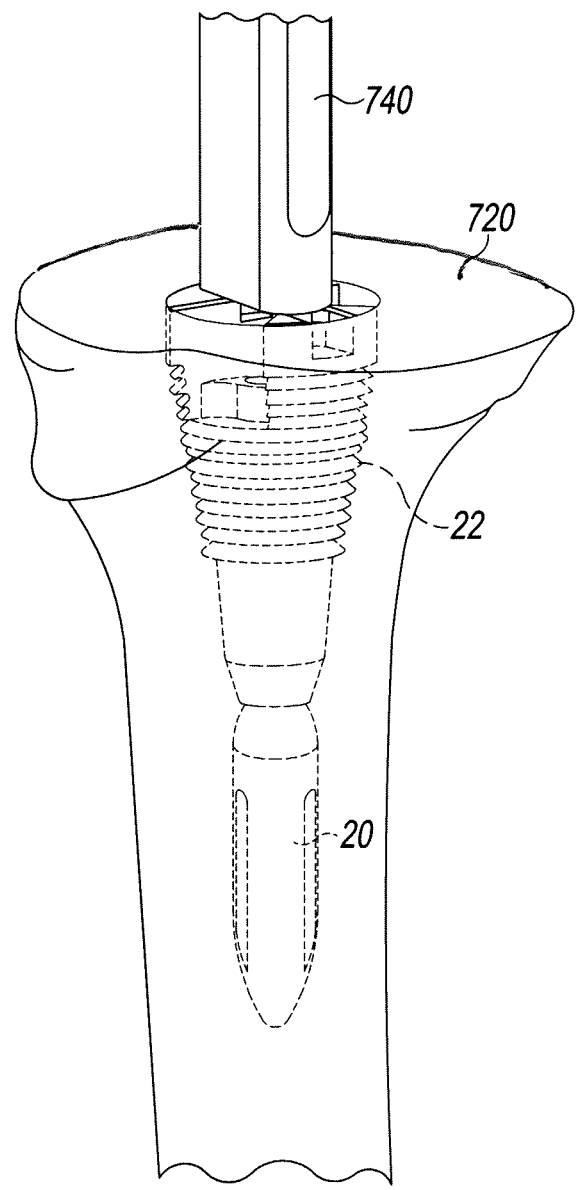
Figure 31:
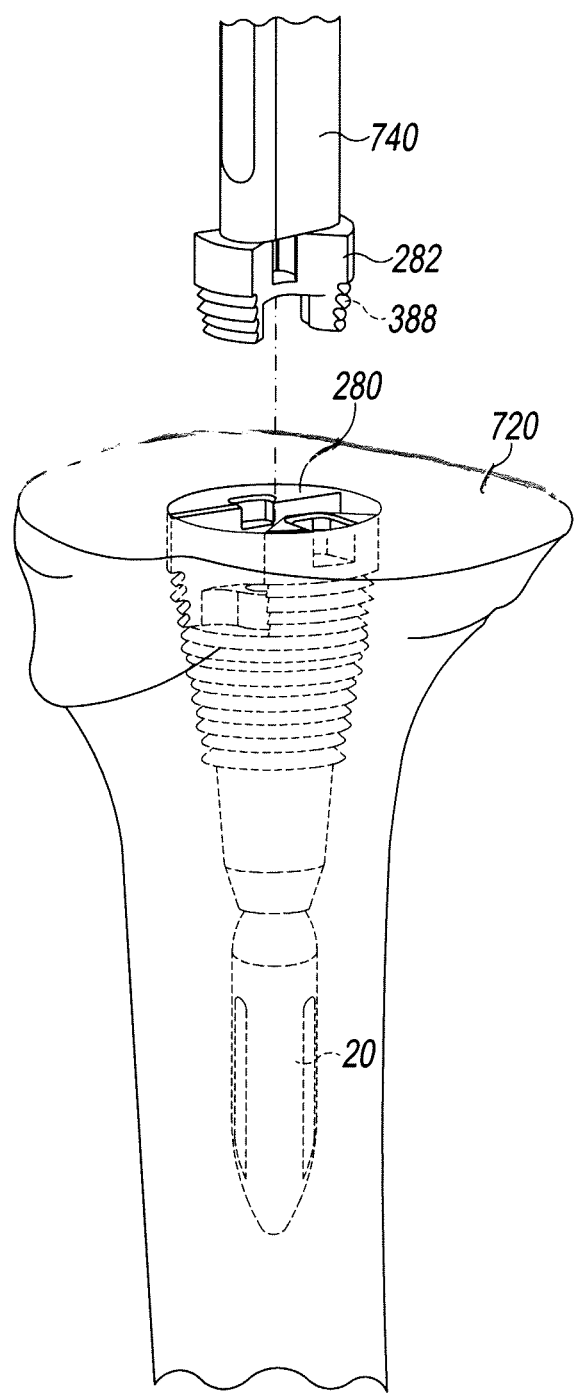
Figure 32:
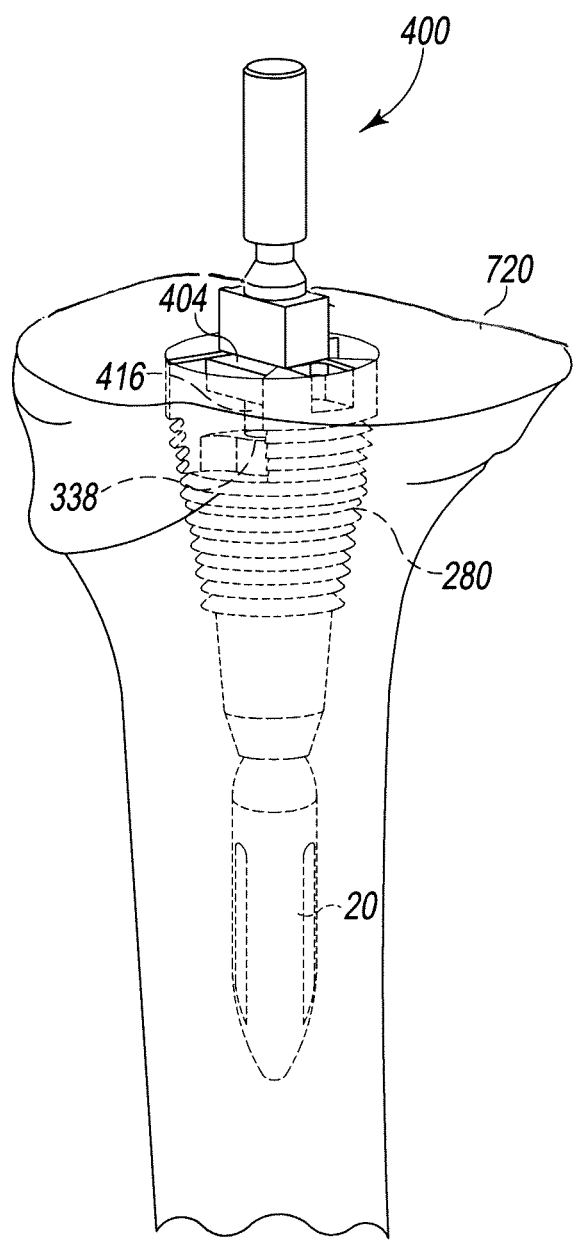

After the intramedullary orthopaedic surgical instrument 16 is assembled in block 806, the procedure 800 advances to procedure block 828. In block 828, the surgeon may advance the stem trial 20 and the broach assembly 22 into the medullary canal 254, as shown in FIG. 30. To do so, the surgeon may secure the broach assembly 22 with the impaction handle 740 by engaging the catch of the impaction handle 740 with the flange 354 of the broach 280. After securing the handle 740 to the broach assembly 22, the surgeon may align the stem trial 20 with the medullary canal 254. The surgeon may then drive the stem trial 20 and the broach assembly 22 into the tibia 720 by striking the handle 740 with mallet, sledge, or other impaction tool. As the broach assembly 22 is driven into the bone, the cutting teeth 290 of the broach 280 and the cutting teeth 388 of the broach insert 282 engage the patient's tibia 720 to shape the medullary canal 254 to receive the prosthetic sleeve.

The procedure 800 may then advance to procedure block 830 in which the surgeon removes the broach insert 282 from the broach 280. To do so, the surgeon may reorient the impaction handle 740 to engage the catch with the flange 380 of the broach insert 282. As shown from the posterior perspective view in FIG. 31, the surgeon may pull the handle 740 in the direction indicated by arrow 758 to disengage the cutting teeth 388 of the broach insert 282 and detach the broach insert 282 from the broach 280.

After the broach insert 282 is removed in block 832, the surgeon may secure the attachment device 12 to the broach 280 in procedure block 832. To do so, the surgeon may attach the adaptor 400 to the broach 280, as shown the posterior perspective view in FIG. 32. The surgeon may align the post 416 of the adaptor 400 with the bore 338 defined in the platform 328 of the broach 280 before advancing the adaptor 400 downward such that the plug 404 is positioned in the slot 316 of the broach 280 and the post 416 is received in the bore 338. The biasing element 418 engages the inner wall 310 of the broach 280 to secure the adaptor 400 to the broach 280. When the adaptor 400 is properly positioned on the broach 280, the base 402 of the adaptor 400 is seated on the top surface 306, and the shaft 422 extends upwardly from the tibia 720.

Figure 33:
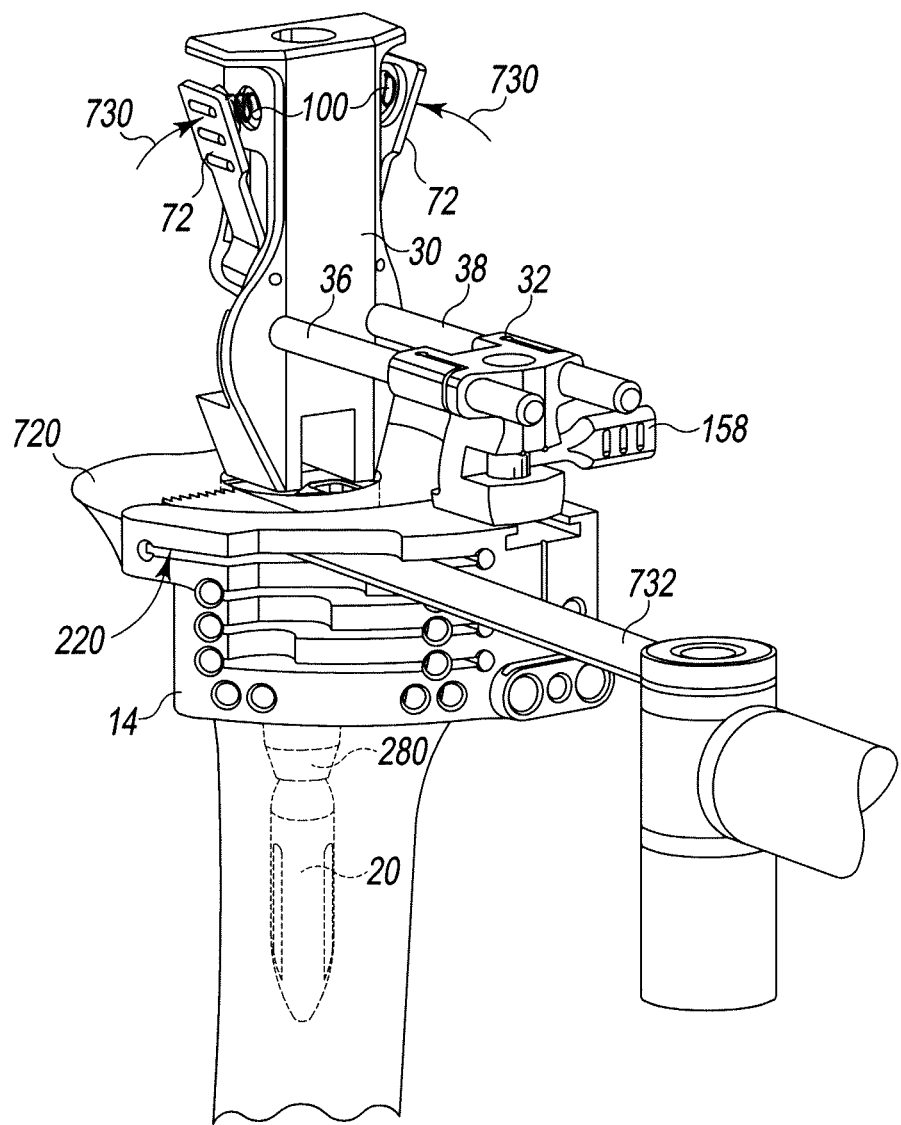

The surgeon may secure the attachment device 12 to the adaptor 400 by aligning the passageway 64 of the attachment base 30 with the shaft 422. The surgeon may then press on the handles 82 of the levers 72 in the direction indicated by arrows 730 in FIG. 33 to rotate the levers 72 and remove the catches 78 from the passageway 64. The surgeon may advance the attachment base 30 downward over the shaft 422 until the lower end 42 of the base 30 engages the plug 404 of the adaptor 400 and the top surface 306 of the broach 280. The surgeon may release the handles 82, thereby permitting the springs 100 to rotate the levers 72 into the engaged position. In that position, the catches 78 are received in the 424 formed in the shaft 422, thereby securing the attachment device 12 to the adaptor 400 (and hence the broach 280).

Returning to FIG. 21B, the procedure may advance to block 814 in which the cutting block 14 is moved into position for the resection of the proximal end 726 of the patient's tibia 720. As described above, the surgeon may secure the cutting block 14 to the mounting frame 32 and position the mounting frame 32 on the rails 36, 38 of the attachment base 30. The surgeon may then move the mounting frame 32 (and hence cutting block 14) into position relative to the tibia 720.

The procedure 800 may then advance to procedure block 834 in which the surgeon performs the resection of the tibia 720. Similar to procedure block 816 described above, the surgeon may use the cutting guides 220 defined in the cutting block 14, as shown in FIG. 24. For example, the surgeon may select the cutting guide 220 of the cutting block 14 corresponding to a desired amount of bone to be removed. The surgeon may perform the resection by inserting a bone saw blade 732 into the selected cutting guide 220 of the cutting block 14. The resection removes a proximal portion of the patient's tibia 720 to create a substantially planar proximal surface 734.

After performing the resection, the surgeon may assemble a tibial tray trial 432 in procedure block 836. To do so, the surgeon may secure the base trial 436 to the broach 280 via the fastener 512. The base trial 436 may aligned with the broach 280 and the lower end 518 of the fastener 512 is advanced into the bore 338. The external threads 522 formed on the fastener 512 are advanced into contact with the internal threads 346 of the broach 280. By rotating the fastener 512 about the longitudinal axis 530 using the button head 514, the internal threads 346 are engaged with external threads 522, thereby securing the broach 280 to the base trial 436. When the base trial 436 is seated on the top surface 306 of the broach 280, the outer sleeve 520 of the fastener 512 is positioned in the bore 338 of the broach 280, and the tibial base trial 436 is engaged with the surgically-prepared proximal surface 734 of the tibia 720.

After the tibial tray trial 432 is positioned, the surgeon may perform a trial reduction in procedure block 822. As described above, the surgeon may position the check insert 570 in the plate opening 450 of the tibial base trial 436 before selecting a trial shim 682 and a tibial bearing surface trial 680. Thereafter, the surgeon may adjust the patient's leg to evaluate performance and ascertain which implant size and configuration (e.g., the thickness of the implant, the mobility of the implant, etc.) will have the best stability in flexion and extension while permitting the desired kinematics. Because the base trial 436 is permitted to rotate relative to the broach 280, the surgeon is able to establish the rotational position of the tibial tray prosthetic component based on the femoral position and best fit coverage of the tibial plateau.

As shown in FIG. 21B, the procedure 800 may advance to procedure block 838 in which the surgeon continues the tibial preparation by impacting the keel punch insert 572 into the proximal end 726 of the tibia 720. Similar to procedure block 824 described above, the surgeon removes the check insert 570 from the base trial 436, as shown in FIG. 28. The surgeon may then secure the punch insert 572 to the attachment tool 566 by aligning the pegs 598, 604 of the attachment tool 566 with the bores 558, 560, respectively, of the punch insert 572 and advancing the pegs 598, 604 into the bores 558, 560.

The surgeon may secure the attachment tool 566 to an impaction handle 740 by engaging a catch (not shown) of the impaction handle 740 with the flange 616 formed on the attachment tool 566. After securing the handle 740 to the tool 566 and the punch insert 572, the surgeon may align the lower arms 574, 576 of the punch insert 572 with the passageways 460, 462 defined in the base trial 436. The surgeon may then advance the punch insert 572 downward such that the lower arms 574, 576 pass through the passageways 460, 462 and into the proximal end 726 of the tibia 720.

The surgeon may then drive the punch insert 572 into the tibia 720 by striking the handle 740 with mallet, sledge, or other impaction tool. As the punch insert 572 is driven into the bone, the cutting teeth 580 of the punch insert 572 engage the patient's tibia 720 to form additional slots (not shown) in the tibia 720. When the punch insert 572 is seated on the tibial base trial 436, the lower arms 574, 576 extend outwardly from the slot 316 defined in the broach 280.

After the keel punch insert 572 has been driven into the tibia 720, the procedure 800 may advance to the procedure block 824. In block 824, the surgeon may remove the tibial tray trial 432 and the punch insert 572 from the proximal end 726 of the patient's tibia 720. To do so, the surgeon may attach a removal tool 750 to the impaction handle 740 and use the removal tool to the tibial base trial 436, the punch insert 572, broach 280, and stem trial 20 from the tibia 720 such that the surgeon may proceed with the implantation of the prosthetic components.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A surgical instrument system for surgically preparing a proximal end of a tibia, the system comprising:
   a surgical reamer including a proximal end, a distal end positioned opposite the proximal end, a plurality of cutting teeth formed at the distal end,
   a housing including an opening sized to receive the proximal end of the surgical reamer and a pair of rails extending transverse to the opening,
   a mounting frame configured to slide along the pair of rails, the mounting frame including a pair of openings sized to receive the pair of rails of the housing and a flange positioned below the pair of openings,
   a cutting block including a channel sized to receive the flange to secure the cutting block to the mounting frame, the cutting block further including a cutting guide sized to receive a cutting tool to resect the proximal end of the tibia to create a surgically-prepared surface, and
   a tibial base trial configured to be positioned on the surgically-prepared surface, the tibial base trial including a slot sized to receive a keel punch.

2. The system of claim 1, further comprising a keel punch sized to extend through the slot defined in the tibial base trial.

3. The system of claim 2, wherein the cutting guide is positioned below the channel of the cutting block.

4. The system of claim 3, wherein the cutting guide further includes an opening defined in an upper surface, and the channel is positioned below the opening.

5. The system of claim 1, further comprising a retention mechanism configured to secure the attachment device to the surgical reamer.

6. A method of surgically preparing a proximal end of a tibia, the method comprising:
   inserting a surgical reamer into a medullary canal of the tibia,
   securing a housing of an attachment device to a proximal end of the surgical reamer,
   aligning a mounting frame with a channel defined in a cutting block including a cutting guide, the channel being positioned above the cutting guide,
   advancing a flange into the channel defined in the cutting block to secure the mounting frame to the cutting block,
   aligning a pair of openings in the mounting frame with a pair of rails of the housing,
   sliding a mounting frame along a pair of rails toward the housing, and
   resecting the proximal end of the tibia using the cutting guide to form a surgically-prepared surface.

7. The method of claim 6, further comprising:
   positioning a tibial base trial on the surgically-prepared surface, and
   inserting a keel punch through a slot defined in the tibial base trial and into the surgically-prepared surface of the tibia.

8. The system of claim 1, further comprising a retention mechanism operable to inhibit movement of the mounting frame relative to the housing.

* * * * *